United States Patent [19]

Roop et al.

[11] Patent Number: 5,958,764
[45] Date of Patent: Sep. 28, 1999

[54] SPECIFIC EXPRESSION VECTORS AND METHODS OF USE

[75] Inventors: Dennis R. Roop; Joseph A. Rothnagel; David A. Greenhalgh, all of Houston, Tex.

[73] Assignee: Baylor College of Medicine, Houston, Tex.

[21] Appl. No.: 08/146,930

[22] Filed: Nov. 1, 1993

Related U.S. Application Data

[63] Continuation-in-part of application No. 08/145,388, Oct. 29, 1993, abandoned, which is a continuation-in-part of application No. 07/876,286, Apr. 30, 1992, abandoned.

[51] Int. Cl.$^6$ .............................. C12N 15/63; C12N 5/00; C12N 15/79

[52] U.S. Cl. ....................... 435/320.1; 435/371; 435/375; 435/69.1; 435/172.3; 935/62; 935/55; 935/34; 935/71

[58] Field of Search .............................. 435/172.3, 240.2, 435/320.1, 371, 375, 69.1; 536/23.1; 935/22, 55, 62, 70, 71, 34

[56] References Cited

U.S. PATENT DOCUMENTS

| | | | |
|---|---|---|---|
| 4,816,464 | 3/1989 | Gilman et al. | 514/299 |
| 4,863,899 | 9/1989 | Todaro | 514/9 |
| 5,008,240 | 4/1991 | Bentz et al. | 514/2 |
| 5,024,841 | 6/1991 | Chu et al. | 424/422 |
| 5,057,411 | 10/1991 | Lancaster et al. | 435/6 |
| 5,057,428 | 10/1991 | Mizutani et al. | 435/285 |
| 5,087,617 | 2/1992 | Smith | 514/44 |
| 5,158,875 | 10/1992 | Miller et al. | 435/69.1 |
| 5,164,304 | 11/1992 | Johnson | 435/69.1 |

OTHER PUBLICATIONS

Bailleul et al., "Skin Hyperkeratosis and Papilloma Formation in Transgenic Mice Expressing a ras Oncogene from a Suprabasal Keratin Promoter," 62 *Cell* 697, 1990.

Blessing et al., "Transgenic Mice as a Model to Study the Role of TGF–β–Related Molecules in Hair Follicles," 7 *Genes & Dev.* 204, 1993.

Christophers et al., "Cellular Architecture of the Stratum Corneum," 56 *J. Invest. Dermator.* 165, 1971.

Cotsarelis et al., "Label–Retaining Cells Reside in the Bulge Area of Pilosebaceous Unit: Implications for Follicular Stem Cells, Hair Cycle, and Skin Carcinogenesis," 61 *Cell* 1329, 1990.

Dale et al., "Assembly of Stratum Corneum Basic Protein and Keratin Filaments in Macrofibrils," 276 *Nature* 729, 1978.

Fenjves et al., "Systemic Distribution of Apolipoprotein E Secreted by Grafts of Epidermal Keratinocytes: Implications for Epidermal Function and Gene Therapy," 86 *Proc. Natl. Acad. Sci. USA* 8803, 1989.

Finch et al., Identification of a Cloned Sequence Activated During Multi–stage Carcinogenesis in Mouse Skin, 12 *Carcinogenesis* 1519, 1991.

Fisher et al., "Localization of Profilaggrin mRNA in Newborn Rat Skin by In Situ Hybridization," 88 *J. Invest. Dermatol.* 661, 1987.

Fuchs et al., "Regulation of Terminal Differentiation of Cultured Human Keratinocytes by Vitamin A," 25 *Cell* 617, 1981.

Garlick et al., "Retrovirus–Mediated Transduction of Cultured Epidermal Keratinocytes," 97 *J. Invest. Dermatol.* 824, 1991.

Goeddel et al., "Expression in *Escherichia coli* of Chemically Synthesized Genes for Human Insulin," 76 *Proc. Natl. Acad. Sci. USA* 106, 1979.

Greenhalgh et al., "Induction of Epidermal Hyperplasia, Hyperkeratosis, and Papillomas in Transgenic Mice by a Targeted v–Ha–ras Oncogene," 7 *Mol. Carcinog.* 99, 1993.

Greenhalgh et al., "Hyperplasia, Hyperkeratosis and Benign Tumor Production in Transgenic Mice by a Targeted v–fos Oncogene Suggest a Role for fos in Epidermal Differentiation and Neoplasia", 8 *Oncogene* 2145, 1993.

Harding et al., "Histidine–rich Proteins (Filaggrins): Structural and Functional Heterogeneity during Epidermal Differentiation," 170 *J. Mol. Biol.* 651, 1983.

Haydock et al., "The Repetitive Structure of the Profilaggrin Gene as Demonstrated Using Epidermal Profilaggrin cDNA," 261 *J. Biol. Chem.* 12520, 1986.

Huff et al., "Identification and Characterization of a Complex Regulatory Array 3' to the Gene Encoding Human Keratin 1," 39 *Clin. Res.* 487A (abstract), 1991.

Huff et al., "Identification of Control Elements 3' to the Human Keratin 1 Gene That Regulate Cell Type and Differentiation–specific Expression," 268(1) *J. Biol. Chem.* 377, 1993.

Huitfeldt et al., "Altered Regulation of Growth and Expression of Differentiation–Associated Keratins in Benign Mouse Skin Tumors," 12 *Carcinogenesis* 2063, 1991.

Iversen et al., "Kinetics of Cell Renewal, Cell Migration and Cell Loss in the Hairless Mouse Dorsal Epidermis," 1 *Cell Tissue Kinet.* 351, 1968.

Itoh et al., "Expression of Hepatitis B Virus Surface Antigen P31 Gene in Yeast," 138 *Biochem. Biophys. Res. Comm.* 268, 1986.

Jansen et al., "Sequence of cDNA Encoding Human Insulin–like Growth Factor I Precursor," 306 *Nature* 609, 1983.

Johnson et al., "Structure of a Gene for the Human Epidermal 67–kDa Keratin," 82 *Proc. Natl. Acad. Sci. USA* 1896, 1985.

Kelly et al., "The B Chain of PDGF Alone is Sufficient for Mitogenesis," 4 *EMBO J.* 3399, 1985.

Knapp et al., "Three cDNA Sequences of Mouse Type I Keratins," 262 *J. Biol. Chem.* 938, 1987.

(List continued on next page.)

Primary Examiner—Jasemine C. Chambers
Assistant Examiner—Karen M. Hauda
Attorney, Agent, or Firm—Lyon & Lyon LLP

[57] ABSTRACT

Gene therapy by using specific expression vectors within the epidermis or epidermal cells. These vectors incorporate regulatory sequences of tissue and differentiation-specific genes.

24 Claims, 11 Drawing Sheets

OTHER PUBLICATIONS von Knebel Doeberitz et al., "Growth–Regulating Functions of Human Papillomavirus Early Gene Products in Cervical Cancer Cells Acting Dominant over Enhanced Epidermal Growth Factor Receptor Expression," 50 *Cancer Research* 3730, 1990.

Krieg et al., "Organization of a Type I Keratin Gene," 260 *J. Biol. Chem.* 5867, 1985.

Lersch et al., 9 *Mol. Cell Biol.* 3685, 1989.

Lersch et al., "Sequence and Expression of a Type II Keratin, K5, in Human Epidermal Cells," 8 *Mol. Cell Biol.* 486, 1988.

Lindahl et al., "Cellular Aspects of Gene Therapy," In: *Growth Factors in Health and Disease*, pp. 383–392, Westermark, Betsholtz and Hökfelt ed., Elsevier Science Publishers B.V., Amsterdam (1990).

MacGregor et al., "Use of *E. coli* lacZ (β–Galactosidase) as a Reporter Gene," In: *Methods in Molecular Biology*, vol. 7: *Gene Transfer and Expression Protocols*, pp. 217–235, E. J. Murray ed., The Humana Press Inc., Clifton, NJ (1991).

MacKenzie et al., "Relationship between Mitosis and the Ordered Structure of the Stratum Corneum in Mouse Epidermis," 226 *Nature* 653, 1970.

Marchuk et al., "Complete Sequence of a Gene Encoding a Human Type I Keratin: Sequences Homologous to Enhancer Elements in the Regulatory Region of the Gene," 82 *Proc. Natl. Acad. Sci. USA* 1609, 1985.

Matoltsky, "Desmosomes, Filaments, and Keratohyalin Granules: Their Role in the Stabilization and Keratinization of the Epidermis," 65 *J. Invest. Dermatol.* 127, 1975.

Mehrel et al., "Identification of a Major Keratinocyte Cell Envelope Protein, Loricrin," 61 *Cell* 1103, 1990.

Morgan et al., "Expression of an Exogenous Growth Hormone Gene by Transplantable Human Epidermal Cells," 237 *Science* 1476, 1987.

Nakazawa et al., "Isolation of a Keratin cDNA Clone Expressed Under Hyperproliferative Conditions," 103 *J. Cell Biol.* 561a, 1986.

Olsen et al., "Human Nidogen: cDNA Cloning, Cellular Expression, and Mapping of the Gene to Chromosome Iq43," 44 *Am. J. Hum. Genet.* 876, 1989.

Potten, "Stem Cells in Epidermis from the Back of the Mouse," In: *Stem Cells: Their Identification and Characterisation*, pp. 200–232, C. S. Potten ed., Churchill Livingstone, Edinburgh (1983).

Rice et al., "The Cornified Envelope of Terminally Differentiated Human Epidermal Keratinocytes Consists of Cross–Linked Protein," 11 *Cell* 417, 1977.

Rieger et al., 204 *J. Mol. Biol.* 841, 1988.

Roop et al., "Transcriptional Control of High Molecular Weight Keratin Gene Expression in Multistage Mouse Skin Carcinogenesis," 48 *Cancer Res.* 3245, 1988.

Roop et al., "Keratin Gene Expression in Mouse Epidermis and Cultured Epidermal Cells," 80 *Proc. Natl. Acad. Sci. USA* 716, 1983.

Rosenberg et al., "Three Epidermal and One Simple Epithelial Type II Keratin Genes Map to Human Chromosome 12," 57 *Cytogenet. Cell Genet.* 33, 1991.

Rosenthal et al., "A Human Epidermal Differentiation–specific Keratin Gene is Regulated by Calcium but not Negative Modulators of Differentiation in Transgenic Mouse Keratinocytes," 2 *Cell Growth and Differentiation* 107, 1991.

Rosenthal et al., "Changes in Photo–Aged Human Skin Following Topical Application of All–Trans Retinoic Acid," 95 *J. Invest. Dermatol.* 510, 1990.

Rothnagel et al., "The Gene for Mouse Epidermal Filaggrin Precursor," 262 *J. Biol. Chem.* 15643, 1987.

Rothnagel et al., "Development of an Epidermal–Specific Expression Vector for Targeting Gene Expression to the Epidermis of Transgenic Mice," 38(2) *Clin. Res.* 688A, 1990.

Rothnagel et al., "Use of Transgenic Mice to Identify Regulatory Sequence 5' to the Human K1 Keratin Gene," 96 *J. Invest. Dermatol.* 541, 1991.

Sambrook et al., "Expression of Proteins from Cloned Genes," *Molecular Cloning: A Laboratory Manual*, published by Cold Spring Harbor Laboratory Press, 2d Edition, 16.3–16.27 (1989).

Schweizer et al., "Sequential Expression of mRNA–Encoded Keratin Sets in Neonatal Mouse Epidermis: Basal Cells with Properties of Terminally Differentiating Cells," 37 *Cell* 159, 1984.

Sellheyer et al., "Inhibition of Skin Development by Overexpression of Transforming Growth Factor $\beta_1$ in the Epidermis of Transgenic Mice," 90 *Proc. Natl. Acad. Sci. USA* 5237, 1993.

Steinert et al., "The Molecular Biology of Intermediate Filaments," 42 *Cell* 411, 1985.

Steinert et al., "Amino Acid Sequences of Mouse and Human Epidermal Type II Keratins of $M_r$ 67,000 Provide a Systematic Basis for the Structural and Functional Diversity of the End Domains of Keratin Intermediate Filament Subunits," 260 *J. Biol. Chem.* 7142, 1985.

Stoler et al., "Use of Monospecific Antisera and cRNA Probes to Localize the Major Changes in Keratin Expression during Normal and Abnormal Epidermal Differentiation," 107 *J. Cell Biol.* 427, 1988.

Takemoto et al., "The Promoter of the endo A Cytokeratin Gene is Activated by a 3' Downstream Enhancer," 19 *Nucl. Acids Res.* 2761, 1991.

Teumer et al., "Human Growth Hormone in the Blood of Athymic Mice Grafted with Cultures of Hormone–Secreting Human Keratinocytes," 4 *FASEB J.* 3245 (1990).

Tomic et al., "Nuclear Receptors for Retinoic Acid and Thyroid Hormone Regulate Transcription of Keratin Genes," 1 *Cell Reg.* 965, 1990.

Tyner et al., 82 *Proc. Natl. Acad. Sci. USA* 4683, 1985.

Tyner and Fuchs, "Evidence for Posttranscriptional Regulation of the Keratins Expressed during Hyperproliferation and Malignant Transformation in Human Epidermis," 103 *J. Cell Biol.* 1945, 1986.

Vassar et al., "Tissue–Specific and Differentiation–Specific Expression of a Human K14 Keratin Gene in Transgenic Mice," 86 *Proc. Natl. Acad. Sci. USA* 1563, 1989.

Weiss et al., "Monoclonal Antibody Analysis of Keratin Expression in Epidermal Diseases: A 48– and 56–kdalton Keratin as Molecular Markers for Hyperproliferative Keratinocytes," 98 *J. Cell Biol.* 1397, 1984.

Williams et al., "Introduction of Foreign Genes into Tissues of Living Mice by DNA–coated Microprojectiles," 88 *Proc. Natl. Acad. Sci. USA* 2726, 1991.

Wood et al., "Expression of Active Human Factor VIII from Recombinant DNA Clones," 312 *Nature* 330, 1984.

Woodcock–Mitchell et al., "Immunolocalization of Keratin Polypeptides in Human Epidermis Using Monoclonal Antibodies," 95 *J. Cell Biol.* 580, 1982.

Yoneda et al., "The Human Loricrin Gene," 267(25) *J. Biol. Chem.* 18060, 1992.

Yoneda et al., "Structure of the Human Loricrin Gene Linkage at 1q21 with Profilaggrin and Involucrin Genes," 39(2) *Clin. Res.* 496A, 1991.

SUPPRESSION OF A NOVEL NEGATIVE REGULATORY ELEMENT FROM
THE HUMAN K1 KERATIN GENE(HK1.NRE)BY VITAMIN $D_3$

[D3]: 0  $10^{-10}$M  $10^{-9}$M  $10^{-8}$M  $10^{-7}$M  $10^{-6}$M

Sequence of HK.1NRE

TGGCCTTGAG$_{10}$GGAGATGATT$_{20}$CACTCTCCTT$_{30}$CACAGAAGAG$_{40}$CTGACCTCTG$_{50}$GGGTCAACAG$_{60}$ATATAGCACC$_{70}$

A new genomic clone containing additional 5' and 3' flaking sequences used to construct the pML.14CAT with the unique EcoRV and Spe I restriction sites.

The original pML.6.5CAT construct.

pML.6.5HK1 showing the location of the human keratin 1 epitope used for in vivo detection of the transgene in transgenic mice.

In vitro expression of the expression vector (pML.14CAT) in primary keratinocytes. Lane 1 pSV2CAT; Lane 2 pA10CAT; Lane 3 pML.14CAT low calcium medium (undifferentiated). Lane 4 pML.14CAT high calcium Medium (differentiated).

Percent CAT activity of the 5' deletion constructs expressed as a ratio of the test plasmid over the activity of the parent pML.CAT in low (0.05mM) and high (0.35 mM) calcium medium respectively.

Percent CAT activity of the 3' deletion constructs expressed as a ratio of the test plasmid over the activity of the parent pML.CAT in low (0.05mM) and high (0.35 mM) calcium medium respectively.

SPECIFIC EXPRESSION VECTORS AND METHODS OF USE

RELATED APPLICATIONS

This application is a continuation-in-part of U.S. patent application Ser. No. 08/145,388 (now abandoned), filed Oct. 29, 1993, entitled "Specific Expression vectors and Methods of Use", by Roop et al. (Lyon & Lyon Docket No. 204/132), which is a continuation-in-part of U.S. patent application Ser. No. 07/876,286 (now abandoned), filed Apr. 30, 1992, entitled "Constitutive and Inducible Epidermal Vector Systems", by Roop et al. (Lyon & Lyon Docket No. 204/017), both of which are incorporated herein by reference in their entirety, including any drawings.

The invention was partially supported by a grant from the United States Government under AR40240 awarded by the National Institutes of Health. The U.S. government may have rights in the invention.

BACKGROUND OF THE INVENTION

This invention relates to gene therapy to cause expression of genes within the epidermis or epidermal cells.

The skin is the largest organ in the human body. The skin consists of two layers, the epidermis and the dermis. The outer layer is the epidermis which is composed of four histologically defined layers, each of which represent a distinct stage of differentiation of the epidermal keratinocyte. The innermost layer is the stratum germinativum (or basal layer) consisting of continuously dividing cells. The next two layers are the stratum spinosum (or spinous layer) and the stratum granulosum (or granular layer). The outermost layer is the stratum corneum consisting of dead cells whose cytoplasm has been entirely replaced by keratin. (Iverson, et al., Cell Tissue Kinet., Vol. 1, pp. 351–367 (1968); MacKenzie, et al., Nature, Vol. 226, pp. 653–655 (1970)).

The dermis lies under the epidermis and is separated from it by a basement membrane. The dermis is a thick layer of living tissue consisting mainly of a loose connective tissue within which are blood capillaries, lymph vessels, sensory nerve endings, sweat glands and their ducts, hair follicles, sebaceous gland and smooth muscle fibers.

The epidermis is a continuously regenerating epithelium. Keratinocytes are the major cell type of the epidermis and arise from the basal cells in the basal layer. The basal cells consist of metabolically active cells. The basal cells are the cells which undergo mitosis. (Potten, In Stem Cells: Their Identification and Characterization, pp. 200–232 (1983)).

Upon commitment to differentiation, the basal cells lose their proliferative potential and migrate to the spinous layer. With further maturation these cells enter the granular layer and finally terminate as cornified squames in the stratum corneum before being sloughed into the environment. (Matoltsky, J. Invest. Dermatol., Vol 65, pp. 127–142 (1975)).

During the regeneration process for the differentiated epidermal cells, the cells express a succession of different homologous keratin genes. The keratin produced by the differentiating cells is an insoluble fibrous protein. Keratins are the most abundant proteins synthesized in the epidermal cells and changes in the keratin expression patterns occur during differentiation.

The degree of differentiation can be defined biochemically by the expression of marker proteins that characterize each stage. (Matoltsky, J. Invest. Dermatol., Vol. 65, pp. 127–42 (1975)). For instance, basal keratinocytes express keratins K5 and K14 as major products. (Woodcock-Mitchell, et al., J. Cell Biol., Vol. 95, pp. 580–88 (1982)). These proteins assemble into 10 nm filaments and together with microtubules and microfilaments, comprise the cytoskeleton of epidermal cells. (Steinert, P. M., et al., Cell, Vol. 42, pp. 411–19 (1985)).

One of the earliest changes associated with the commitment to differentiation and migration into the spinous layer is the induction of another differentiation-specific pair of keratins, K1 and K10. Once a cell is committed to the differentiation pathway the cells downregulate the genes for K5 and K14, and express the genes for the differentiation-specific keratins, K1 and K10. (Woodcock-Mitchell, et al., J. Cell Biol., Vol. 95, pp. 580–88 (1982); Roop, et al., Proc. Natl. Acad. Sci., USA, Vol. 80, pp. 716–20 (1983); Schweizer, et al., Cell, Vol. 37, pp. 159–170 (1984)). Transcription of K1 and K10 is restricted to the spinous layer cells. The expression of K1 precedes K10 and is one of the earliest in keratinocyte differentiation. Occasionally, K1 can be observed in a basal cell that has already ceased mitotic activity and is about to migrate into the spinous layer. Haitfeld et al. Carcinogenesis, 12 pp. 2063–2067 (1991). When the cells mature into granular layer cells, the genes for K1 and K10 are downregulated. At this point, other genes, notably loricrin and filaggrin, are induced. (Dale, B. A., et al., Nature, Vol. 276, pp. 729–731 (1978); Harding, C. R., et al., J. Mol. Biol., Vol. 170, pp. 651–673 (1983)).

Genes or cDNAs encoding the major keratins expressed in epidermal cells have been cloned, such as K5 (Lersch, et al., Mol. and Cell Biol., Vol. 8, pp. 486–493 (1988)), K14 (Marchuk, et al., Proc. Natl. Acad. Sci., USA, Vol. 82, pp. 1609–1613 (1985); Knapp, et al., J. Biol. Chem., Vol. 262, pp. 938–945 (1987); Roop, et al., Cancer Res., Vol. 48, pp. 3245–3252 (1988)), K1 (Steinert, et al., J. Biol. Chem., Vol. 260, pp. 7142–7149 (1985)), and K10 (Krieg, et al., J. Biol. Chem., Vol. 260, pp. 5867–5870 (1985)). In addition, human K6 cDNA has been cloned. (Tyner, et al., Proc. Natl. Acad. Sci., USA, Vol. 82, pp. 4683–4687 (1985)).

Northern blot analysis and in situ hybridization studies suggest that keratin genes K5 and K14 are predominantly transcribed in the proliferating basal layer. Transcription of keratin genes K1 and K10 is induced as cells migrate into the spinous layer. (Lersch, et al., Mol. and Cell Biol., Vol. 8, pp. 486–493 (1988); Knapp, et al., J. Biol. Chem., Vol. 262, pp. 938–945 (1987); Roop, et al., Cancer Res., Vol. 48, pp. 3245–3252 (1988)). K6 is expressed in human skin under conditions of high proliferation and malignant transformation. (Tyner, et al., J. Cell Biol., Vol. 103, pp. 1945–1955 (1986)).

Genes encoding rat and mouse filaggrin have also been identified. In situ hybridization experiments confirmed that transcription of this gene is restricted to the granular layer. (Haydock, et al., J. Biol. Chem., Vol. 261, pp. 12520–12525 (1986); Rothnagel, et al., J. Biol. Chem., Vol. 262, pp. 15643–15648 (1987); Fisher, et al., J. Invest. Dermatol., Vol. 88, pp. 661–664 (1987)).

Loricrin, one of the genes encoding a component of a cornified envelope, has been studied at the molecular level by in situ hybridization showing that transcripts of this gene are restricted to the granular layer. (Mehrel, et al., Cell, Vol. 61, pp. 1103–1112 (1990)). Both the human loricrin gene (Yoneda, et al., J. Biol. Chem., Vol. 267, no. 25, pp. 18060–18066 (1992)), and the mouse loricrin cDNA (Mehrel, et al., Cell, Vol. 61, pp. 1103–1112 (1990)) have been isolated and cloned.

Studies have shown that cells generated by cultivation of a small biopsy can be prepared as stratified sheets and then used for replacement of damaged skin by grafting techniques. (Lindahl, et al., Growth Factors in Health and Disease, p. 388 (1990)). Other studies describe genetically engineered keratinocytes which synthesize human growth hormone. (Morgan, et al., Science, Vol. 237, pp. 1476–1479 (1987)). These studies described retrovirus mediated gene transfer to introduce recombinant human growth hormone into cultured human keratinocytes. The retroviruses were generated from the ΨAM cell line using an SV40 promoter. (Morgan, et al., Science, Vol. 237, pp. 1476–1479 (1987); Teumer, et al., Growth Hormone and Athymic Mice, FASEB, Vol. 4, pp. 3245–3250 (1990)). The transduced keratinocyte cultures secreted human growth hormone.

In addition, other studies have shown human keratinocytes permanently transformed with plasmids containing the human growth hormone gene under the control of either the metallothionein promoter or the herpesvirus thymidine kinase promoter. (Lindahl, et al., Growth Factors in Health and Disease, p. 388 (1990)). These studies also described skin grafting techniques with the genetically engineered keratinocytes.

SUMMARY OF THE INVENTION

Applicant has determined that it is useful to construct vectors based upon epidermal-specific genes. Specifically, expression of these vectors is tissue and differentiation-specific. These are useful in targeting the epidermis through different stages of differentiation. These vectors can be used to treat diseases by targeting the vector accordingly. These vectors can also be used to create transgenic animals for assessing human disease in an animal model.

Keratin genes are expressed in the epidermis in a differentiation-specific manner. The regulatory elements of such keratin genes are useful for tissue and differentiation-specific target vectors. Keratins K5 and K14 are expressed in the epidermal proliferative compartment, whereas keratins K1 and K10 are associated with early differentiation. Occasionally, K1 can be observed in a basal cell that has already ceased mitotic activity and is about to migrate into the spinous layer. K6 is present in the epidermis but expressed only under high proliferation conditions or in the hair follicles. In addition, filaggrin and loricrin are associated with late differentiation. By using the regulatory elements of these and other such genes, specific expression vectors can be constructed to target the expression of particular nucleic acids in a tissue and differentiation-specific manner.

The 5' regulatory regions of four human epidermal keratin genes, K5, K6, K10 and K14, have been cloned into vectors to drive expression of the CAT reporter gene. These constructs were transfected into epithelial cells along with vectors expressing nuclear receptors for retinoic acid and thyroid hormone. (Tomic, et al., Cell Reg., Vol. 1, pp. 965–973 (1990)). This study demonstrated that these receptors can suppress the promoters of keratin genes. Suppression was ligand dependent and was evident in primary cultures of epithelial cells. Other studies have discussed the regulation by calcium of human keratin genes K1 and K10. (Rosenthal, et al., Cell Growth and Differentiation, Vol. 2, pp. 107–113 (1991)). 5' and 3' flanking sequence for the human K1 gene responded to elevated levels of calcium in order to induce both mouse K1 and human K1 expression.

Furthermore, both the 5' and 3' sequences for human K1 keratin gene have been used to express oncogenes exclusively to the epidermis of transgenic mice. (Greenhalgh, et al., Mol. Carcinogenesis, Vol. 7, pp. 99–110 (1993); Greenhalgh, et al., Oncogene, Vol. 8, pp. 2145–2157 (1993)). The control elements of 5' and 3' flanking sequences of the human keratin K1 gene that respond to calcium and differentiation were studied by mutations to the 5' and 3' sequences. These studies further define DNA regulatory elements for calcium induced differentiation responses. (Huff, et al., J. Biol. Chem., Vol. 268, No. 1, pp. 377–384 (1993)).

Other expression vectors have been constructed with the K1 5' and 3' sequences to target TGF-β to the epidermis. This study involved the role of TGF-β as an inhibitor of epithelial-cell proliferation. (Sellheyer, et al., PNAS, Vol. 90, pp. 5237–5241 (1993)). In addition, a bovine K6 vector was also constructed to study the role of TGF-β in hair follicles. (Blessing, et al., Genes & Dev., Vol. 7, pp. 204–215 (1993)).

Taking advantage of the unique targeting ability of epidermal cells, the present invention features use of the loricrin regulatory regions and the keratin K6 gene regulatory regions to construct vectors which direct efficient expression of exogenous DNA in epidermal cells. In particular, the present invention demonstrates that by removing sequences that normally restrict expression of the loricrin gene to differentiated cells an expression vector can be constructed which achieves high levels of expression in undifferentiated epidermal cells. Such expression is greater than equivalent vectors which use the viral promoter SV40. The vector can be constitutively expressed in epidermal cells at all differentiation states, not just the granular layer. Likewise, if the sequences that normally restrict expression of a loricrin gene are not removed, an expression vector may be constructed which directs expression of exogenous DNA to only cells of the differentiated layers of the epidermis.

In addition, the present invention takes advantage of the expression characteristics of the K6 gene which is normally not expressed in the epidermis but, is induced under conditions which induce a high level of proliferation, such as during wound healing, after topical application of retinoic acid, and that associated with malignant transformation. Advantage is also taken of K6 expression in hair follicles. Using the K6 regulatory elements, vectors can be constructed in which gene expression can be induced under high proliferative conditions, or expressed in the hair follicle.

This unique targeting ability also allows transgenic animal models used for not only the dissection of molecular carcinogenesis and disease, but also in assessing potential chemical and physical carcinogens and tumor promoters, and exploring novel therapeutic avenues. Furthermore, advantages due to the unique targeting ability of the above vectors allow methods to administer and treat wounds, surgical incisions, skin ulcers, psoriasis, cancer and alopecia. Furthermore, the above vectors can be used to transform epidermal cells to produce particular proteins, polypeptides, and RNA, as well as be used in methods for creating immune responses.

Likewise, the above expression vectors can be used in vitro with epidermal cells in culture. Use of these vectors in vitro allows the role of various nucleic acids to be studied by target specific expression into epidermal cells. (Greenhalgh, et al., Mol. Carcinogenesis, Vol. 7, pp. 99–110 (1993); Greenhalgh, et al., Oncogene, Vol. 8, pp. 2145–2157 (1993)).

It should also be noted that this invention features vectors using the regulatory elements required for specific nucleic acid expression in epidermal cells, including regulatory elements from the K1, K6 and loricrin genes, as well as other regulatory elements of specific genes which are not K1, K6 or loricrin.

In the first aspect, the present invention features a vector for expression of a nucleic acid sequence in an epidermal cell. The vector includes a 5' flanking region which includes necessary sequences for expression of a nucleic acid cassette, a 3' flanking region which regulates expression of a nucleic acid sequence, predominantly in the epidermis, and a linker which connects the 5' flanking region to a nucleic acid. The linker has a position for inserting a nucleic acid cassette. The linker does not contain the coding sequence of a gene that the linker is naturally associated with. That is, the linker is not the normal gene associated with the 5' and 3' regions. The term epidermal cell as used herein refers to those cells of the epidermis and dermis, but also includes the hair follicles and related cells.

The term "vector" as used herein refers to a nucleic acid, e.g., DNA derived from a plasmid, cosmid, phasmid or bacteriophage, into which fragments of nucleic acid may be inserted or cloned. The vector can contain one or more unique restriction sites for this purpose, and may be capable of autonomous replication in a defined host or organism such that the cloned sequence is reproduced. The vector molecule can confer some well-defined phenotype on the host organism which is either selectable or readily detected. Some components of a vector may be a DNA molecule incorporating DNA, a sequence encoding a therapeutic or desired product, and regulatory elements for transcription, translation, RNA stability and replication. A viral vector in this sense is one that contains a portion of a viral genome, e.g. a packaging signal, and is not merely DNA or a located gene within a viral particle.

The purpose of the vector is for expression of a nucleic acid sequence in an epidermal cell. Expression includes the efficient transcription of an inserted gene or nucleic acid sequence within the vector. Expression products may be proteins, polypeptides or RNA. The gene insert or nucleic acid sequence is contained in the nucleic acid cassette.

The term "nucleic acid cassette" as used herein refers to the genetic material of interest which can express a protein, polypeptide or RNA. The nucleic acid cassette is positionally and sequentially oriented within the vector such that the nucleic acid in the cassette can be transcribed into RNA, and when necessary, translated into a protein or a polypeptide in the transformed epidermal cell. Preferably, the cassette has its 3' and 5' ends adapted for ready insertion into a vector, e.g., it has restriction endonuclease sites at each end.

A variety of proteins and polypeptides can be encoded by the sequence in a nucleic acid cassette in the transformed epidermal cells. Those proteins or polypeptides which can be expressed include hormones, growth factors, enzymes, clotting factors, apolipoproteins, receptors, drugs, oncogenes, tumor antigens, tumor suppressors, viral antigens, parasitic antigens and bacterial antigens. Specific examples of these compounds include proinsulin, insulin, growth hormone, androgen receptors, insulin-like growth factor I, insulin-like growth factor II, insulin growth factor binding protein, epidermal growth factor TGF-α, TGF-β, dermal growth factor (PDGF), angiogenesis factors (acidic fibroblast growth factor, basic fibroblast growth factor and angiogenin), matrix proteins (Type IV collagen, Type VII collagen, laminin), oncogenes (ras, fos, myc, erb, src, sis, jun), E6 or E7 transforming sequence, p53 protein, cytokine receptor, IL-1, IL-6, IL-8, viral capsid protein, and proteins from viral, bacterial and parasitic organisms which can be used to induce an immunologic response. In addition, the nucleic acid cassette can code for antisense RNA or ribozymes as well. These are only examples and are not meant to be limiting in any way.

The term "flanking region" as used herein refers to nucleotide sequences on either side of an associated gene. Flanking regions can be either 3' or 5' to a particular gene in question. In general, flanking sequences contain elements necessary for regulation of expression of a particular gene. This can include regulatory sequences necessary for tissue-specific expression, differentiation-specific expression, as well as sequences necessary for efficient expression.

Usually, specific regulatory sequences or elements are embedded adjacent to or within the protein coding regions of DNA. These elements, located adjacent to the gene, are termed cis-acting elements. The signals are recognized by other diffusible biomolecules in trans to potentiate the transcriptional activity. These biomolecules are termed "trans-acting factors". The presence of the trans-acting factors and cis-acting elements have been shown to contribute to the timing and developmental expression pattern of a gene. Cis-acting elements are usually thought of as those that regulate transcription and are found within promoter regions and other upstream (5') or downstream (3') DNA flanking regions.

Flanking DNA with regulatory elements that regulate expression of the genes of the epidermis may also include modulator sequences that are regulated by specific factors, such as Vitamin $D_3$ and its metabolites, Vitamin A and its metabolites, retinoic acid and calcium as well as others. "Modulator sequences" as used herein refers to sequences which may be in the 3' or 5' flanking region, where such sequence can enhance activation and/or suppression of the transcription of the associated gene. "Responsive" or "respond" as used herein in relation to modulate relates to the enhancement of activation and/or suppression of gene transcription as discussed below. Metabolite as used herein refers to any product of metabolism.

The 5' flanking regions may include a promoter, a TATA box, a CAP site and a first intron and intron/exon boundary which are in an appropriate relationship sequentially and positionally for the expression of an associated gene. In this invention, "necessary sequences" are those elements of the 5' flanking region which are sequentially and positionally in an appropriate relationship to cause the specific expression of a nucleic acid cassette. The 5' flanking region can provide tissue-specific expression to an associated gene.

The 5' sequence may contain elements which regulate tissue-specific expression. The 5' flanking region is located 5' to the associated gene or nucleic acid sequence to be expressed. The 5' flanking region regulatory elements can include the portion of a naturally occurring 5' element responsible for tissue-specific expression. The 5' flanking region can be defined by known procedures. For example, the active portion of the 5' flanking region can be mapped by mutational analysis or various clones created to define the desired activity in a selected vector.

The term "promoter" as used herein refers to a recognition site of a DNA strand to which the RNA polymerase binds. The promoter usually is a DNA fragment of about 100 to 200 base pairs (in eucaryotic genes) in the 5' flanking DNA upstream of the CAP site or the transcriptional initiation start site. The promoter forms an initiation complex with RNA polymerase to initiate and drive transcriptional activity. The complex can be modified by activating sequences termed "enhancers" or inhibitory sequences termed "silencers". The promoter can be one which is naturally or non-naturally associated with a 5' flanking region.

The term "intron" as used herein refers to a section of DNA occurring in a portion of a gene which does not code for an amino acid in the gene product. RNA transcribed from such an intron is included in a precursor RNA, from which the intron mRNA is then excised (and is therefore not transcribed into messenger RNA nor translated into protein).

The term "exon" as used herein refers to a portion of a gene that is included in the transcript of a gene and survives processing of the RNA in the cell to become part of a messenger RNA. Exons generally occupy three distinct regions of genes that encode proteins. The first, which is not translated into proteins, signals the beginning of RNA transcription and contains sequences that direct the messenger RNA to the ribosomes for protein synthesis. The exons in the second region contain the information that is translated into the amino acid sequence of the protein. Exons in the third region are transcribed into the part of the messenger RNA that contains the signals for termination of translation and for the addition of polyadenylation tail (poly(A)).

The intron/exon boundary will be that portion in a particular gene where an intron section connects to an exon position. The terms "TATA box" and "CAP site" are used as they are recognized in the art.

The 3' flanking region contains sequences which regulate expression predominantly in the epidermal cells of a nucleic acid sequence. The 3' flanking regions provide tissue-specific expression to an associated gene. The 3' flanking region may be located within a vector of this invention either 5' or 3' to that of an associated gene in order to regulate its expression. The term as used herein includes that portion of the naturally occurring 3' flanking region responsible for tissue-specific expression. That portion can be readily defined by known procedures. For example, the active portions of a 3' flanking region can be mapped by mutational analysis or various clones created to define the desired activity in a selected vector system.

By "gene", e.g., "keratin gene" is meant those genes exemplified herein and their equivalents in other animal species or other tissues. Homologous or analogous sequences are also included so long as they provide equivalent regulatory properties to those described herein. It is important in this invention that the chosen sequence provide the tissue specific expression noted herein. In addition, other sequences such as the modulators and regulators noted herein include such analogous sequences and functionalities. Those in the art will recognize that the minimum sequences required for such a function are encompassed by such a definition and are readily determined by standard technique exemplified herein.

The 3' flanking region may also contain a 3' untranslated region or 3' UTR. This term refers to the sequence at the 3' end of a structural gene which is usually transcribed with the gene. This 3' UTR region usually contains a poly(A) sequence. Although the 3' UTR is transcribed from the DNA, it is not translated into protein. Keratin-specific 3' UTR sequences may be used to allow for specific stability in a keratinocyte or epidermal tissues.

A "3' non-coding region" or "NCR" is a region contiguous to the 3' UTR region of a structural gene. The 3'-NCR region generally contains a transcriptional termination signal.

The 3' UTR and NCR sequences can provide a higher level of messenger RNA accumulation through increased messenger RNA stability in keratinocytes rather than non-keratinocyte cells. Thus, this increased stability of messenger RNA leads to increased levels of protein production. It should also be noted that the 5' flanking region can also contain UTR and NCR sequences.

The 3' flanking regions from keratin genes regulate expression predominantly in the epidermis. "Predominantly" as used herein means that the gene associated with the 3' flanking region, whether natural or in the expression vector, will be expressed to a higher degree only in the epidermis, i.e., to the same order of magnitude of difference as would be found in natural expression of the Keratin genes in the epidermis versus other cell types. In addition, the same magnitude of difference may be observed in an epidermal vs. other cell types such as muscle. Such differences can be observed by Northern analysis, X-gal immunofluorescence or CAT assays as discussed herein and as known in the art. While keratin genes are normally expressed in the epidermis or epidermal cells, namely, keratinocytes, keratin genes are expressed to a lower degree in other tissues, such as the oral mucosa, esophagus and trachea, and other tissues as well. The 3' flanking region as used herein will also express the associated gene in other tissues but to a lower degree than expression in the epidermis. Expression is preferentially in the epidermis.

The term "linker" as used herein refers to DNA which contains the recognition site for a specific restriction endonuclease. Linkers may be connected to the ends of DNA fragments prepared by cleavage with some other enzyme. A linker having a unique restriction endonuclease site at the location of the start and stop codon connects the 5' flanking region to a nucleic acid. In particular, the linker provides a position for inserting the nucleic acid cassette which contains a specific nucleic acid sequence to be expressed. This position may be an endonuclease site in the linker, such as Cla I, Not I, Xma I, Bgl II, Pac I, Xho I, Nhe I and Sfi I.

In preferred embodiments, the vector described above may have as its 5' flanking region and/or its 3' flanking region those regions from either a loricrin gene or a K6 keratin gene. In particular, the present invention may have a 5' flanking region of approximately 1.5 kb, an intron and intron/exon boundary of approximately 1.1 kb and a 3' flanking sequence of approximately 2.1 kb of a loricrin gene. Likewise, the vector may contain a 5' flanking region of approximately 8.0 kb, the intron and intron/exon boundary of approximately 0.56 kb and the 3' flanking region of approximately 1.2 kb of a K6 keratin gene.

As discussed above, these regions can be further and more precisely defined by routine methodology. Preferably, the vector contains such a 3' region or 5' region comprising, consisting, or consisting essentially of these regions. The term "consisting of" is used herein as it is recognized in the art. A vector with the 3' or 5' regions "consisting essentially of" the regions of the present invention includes those regions in which the sequence is changed, but the desired vector activity remains equivalent. Such a change, for example, could be a change of 10 nucleotides in any of the above regions. This is only an example and is non-limiting.

More particularly, the vector above, may contain a 5' flanking region having nucleotides 1 to 1540 of Sequence ID No. 1, an intron and intron/exon boundary having nucleotides 1587 to 1679 of Sequence ID No. 1, a 3' flanking region having nucleotides 4384 to 6530 of Sequence ID No. 1, and a linker inserted at a unique Cla I site at nucleotides 2700 to 2705 of Sequence ID No. 2.

In addition, a more particular aspect of the above vector may contain a 5' flanking region having a unique 5' Xho I site up to nucleotide 360 of Sequence ID No. 3, an intron and intron/exon boundary having nucleotides 928 to 1494 of Sequence ID No. 3, a flanking region having from nucleotide 4740 of Sequence ID No. 3 to a unique 3' Xho I site, and a linker inserted between nucleotides 1504 to 1509 of Sequence ID No. 3.

The invention can also feature a vector as described above with 5' UTR sequences, 3' UTR sequences, and 3' NCR sequences. These can be incorporated into the vector to allow the nucleic acid in the cassette to be transcribed into RNA and then when necessary, translated into proteins or polypeptides in the transformed epidermal cell.

A second aspect of the present invention is a purified nucleic acid sequence comprising the 5' flanking region and the 3' flanking region of Sequence ID No. 1. In addition, another aspect is a purified nucleic acid sequence comprising a 5' flanking region and a 3' flanking region of Sequence ID No. 3. "Purified" as used herein means that the sequence is isolated from its natural state. The present invention also covers the 5' flanking region or the 3' flanking region by themselves. Not only does the invention cover either of the 5' flanking region or 3' flanking region of the loricrin or K6 gene, but other equivalent genes as well.

In a third related aspect, the present invention features an epidermal cell transformed with a vector as described above for expression of a nucleic acid sequence. As described above, the nucleic acid cassette may contain genetic material encoding for a variety of proteins, polypeptides or RNA.

As used herein, "transformation" is a mechanism of gene transfer which involves the uptake of DNA by a cell or organism. Following entry into the cell, the transforming DNA may recombine with that of the host or may replicate independently as a plasmid or temperate phage. Cells which are able to take up DNA are described as competent. Particular cells may not be naturally competent, but require various treatments in order to induce the transfer of DNA across the cell membrane.

Transformation can be performed by in vivo techniques as described below, or by ex vivo techniques in which epidermal cells are co-transfected with a vector containing a selectable marker. This selectable marker is used to select those cells which have become transformed. It is well known to those skilled in the art the type of selectable markers to be used with transformation studies.

The transformed cell can produce a variety of compounds selected from proteins, polypeptides or RNA, including hormones, growth factors, enzymes, clotting factors, apolipoproteins, receptors, drugs, tumor antigens, viral antigens, parasitic antigens and bacterial antigens. Other examples can be found above in the discussion of nucleic acid cassettes. The product expressed by the transformed cell depends on the nucleic acid of the nucleic acid cassette. As discussed above, this is only an example and is not meant to be limiting.

A fourth aspect of the present invention features methods for transformation of epidermal cells. These methods comprise the steps of contacting a cell with a vector as described above for a sufficient time to transform the epidermal cell.

In a fifth aspect, the present invention features a method for treating a wound or surgical incision. In addition, the present invention features a method to treat skin ulcers. These methods use the above-referenced vectors in order to transform epidermal cells. The nucleic acid cassette of the vector contains genetic material coding for a growth factor, a matrix protein or angiogenesis factor. Expression of such genes in vivo aids in the treatment of wounds or surgical incisions. As above, the methods of transformation can be by in vivo or ex vivo techniques.

In a more particular related aspect, the methods involve transforming epidermal cells with a plurality of the above-referenced vectors. In these particular methods, the genetic material of at least one vector codes for a growth factor, the genetic material of at least one vector codes for a second growth factor, the genetic material of at least one vector codes for a matrix protein and the genetic material of at least one vector codes for an angiogenesis factor. The growth factors may consist of epidermal growth factor, transforming growth factor, dermal growth factor or even growth hormone. The matrix protein may consist of Type IV collagen, laminin, nidogen or Type VII collagen. The angiogenesis factor may consist of acidic fibroblast growth factor, basic fibroblast growth factor and angiogenin.

Transformation in these methods and those below can be performed by in vivo techniques, as well as ex vivo techniques. Ex vivo techniques also can include transplanting the transformed epidermal cells into the animal or human to be treated. Such an ex vivo procedure is used with treating wounds or surgical incisions or skin ulcers and other methods below.

A sixth related aspect of the present invention features a method for treating psoriasis by transforming epidermal cells with the above-referenced vectors. These vectors contain nucleic acid sequences coding for proteins, polypeptides or RNA, such as transforming growth factors or cytokine receptors. The RNA which is produced by the expression vector may be antisense RNA complementary to transforming growth factor alpha, IL-1, IL-6 or IL-8. The cytokine receptors may be receptors for IL-1, IL-6 or IL-8. "Receptor" as used herein includes natural receptors as well as anything that binds a ligand and causes compartmentalization changes in a cell.

A seventh related aspect of the present invention features a method for treating cancer. This method includes the transformation of squamous epithelial cells with the above-referenced vectors. The nucleic acid cassettes of the above vectors contain genetic material coding for proteins, polypeptides or RNA. In particular, the genetic material may code for the p53 protein or code for antisense RNA which is complementary to the E6 or E7 gene of human papilloma virus.

Squamous epithelial cells as used herein, are cells which may be either epidermis cells, oral mucosal, esophageal, vaginal, trachea or corneal epithelia.

An eighth related aspect of the present invention features a method for treating alopecia. This treatment includes the transformation of epidermal cells with above-referenced vectors. The nucleic acid sequence of these vectors contain genetic material coding for dominant negative forms of the androgen receptors, epimorphin or angiogenesis factors. The nucleic acid cassette may contain genetic material coding for antisense RNA complementary to 5-α-reductase or an androgen receptor. The angiogenesis factors which may be expressed could be acidic fibroblast growth factor, basic fibroblast, angiogenin or transforming growth factor alpha.

A ninth related aspect of the present invention features a method for inducing an immunogenic or immunological response by transforming an epidermal cell with the above-referenced vectors. The nucleic acid cassette may contain nucleic acid sequences coding for proteins or polypeptides, or other factors which might produce an immunogenic or immunological response. The nucleic acid cassette can contain genetic material that encodes for microbial proteins.

This includes genetic material coding for a viral capsid protein from the human papilloma virus, other viral capsids, bacterial proteins and toxins. This is only an example and is not meant to be limiting.

A tenth related aspect of the invention features a transgenic animal whose cells contain the vectors referenced above. These cells include germ or somatic cells. Transgenic animal models can be used for not only dissection of molecular carcinogenesis and disease, but also in assessing potential chemical and physical carcinogens and tumor promoters, and exploring novel therapeutic avenues.

The genetic material which is incorporated into the epidermal cells from the above vectors includes DNA not normally found in epidermal cells, DNA which is normally found in epidermal cells but not expressed at physiological significant levels, DNA normally found in epidermal cells and normally expressed at physiological desired levels, and other DNA which can be modified for expression in epidermal cells, and any combination of the above.

The vectors of the above methods may be administered by various routes. The term "administration" refers to the route of introduction of a vector or carrier of DNA into the body. Administration may be intravenous, intramuscular, topical, oral, or by gene gun or hypospray instrumentation. Administration can be directly to a target tissue or through systemic delivery. Administration will include a variety of methods, such as direct gene transfer into skin tissue by liposomes, proteoliposomes, calcium phosphate-coprecipitated DNA, DNA coupled to macromolecular complexes, DNA transporters, DNA coded to microprojectiles, coded plasmids, direct microinjection, as well as skin grafts. Direct gene transfer of vectors can be administered by direct microinjection, electroporation, liposomes, proteoliposomes, calcium phosphate-coprecipitation, skin grafts, retroviral vectors, DNA coupled to macromolecular complexes, DNA transporters and microprojectiles. Routes of administration include intramuscular, aerosol, oral, topical, systemic, ocular, intraperitoneal and/or intrathecal. See, e.g., WO 93/18759, hereby incorporated by reference herein.

Other features and advantages of the invention will be apparent from the following detailed description of the invention in conjunction with the accompanying drawings and from the claims.

The drawings are not necessarily to scale, and certain features of the invention may be exaggerated in scale and shown in schematic form in the interest of clarity and conciseness.

DETAILED DESCRIPTION OF THE INVENTION

The following are examples of the present invention using the regulatory elements of the loricrin gene, the K6 keratin gene, or the K1 keratin gene to construct vectors for specific nucleic acid expression in epidermal cells. These examples are offered by way of illustration and are not intended to limit the invention in any manner.

The following are specific examples of preferred embodiments of the present invention. These examples demonstrate how keratin- and loricrin-based vectors can be used in construction of various cellular or animal models, and how genes can be regulated by sequences within such vectors. The utility of such vectors is noted herein and is amplified upon in co-pending application by Roop et al., entitled "Keratin K1 Expression Vectors and Methods of Use", supra, and such sections are hereby specifically incorporated by reference herein.

Below are provided examples of specific regions of the keratin and loricrin genes that can be used to provide certain functionalities to an expression vector, and thus within a transformed cell or animal containing such a vector. Those in the art will recognize that specific portions of these regions can be identified as that containing the functional nucleic acid sequence providing the desirable property, and such regions can be readily minimized using routine deletion or mutagenic techniques or their equivalent. Thus, such regions include the modulator sequence described below, as well as those sequences responsive to calcium, Vitamin D and its metabolite, Vitamin A and its metabolite, and progesterone. As noted herein, such controlling segments of nucleic acid may be inserted at any location on the vector, although there may be preferable sites as described herein.

EXAMPLE 1

Loricrin Gene

Although loricrin is a major keratinocyte cell envelope protein, it was not identified until 1990 (Mehrel, et al., Cell, Vol. 61, pp. 1103–1112 (1990)). The primary sequence of the loricrin protein was deduced from the overlapping cDNA clones described in Mehrel, id. To obtain the full gene, the cDNA clones were used to screen an EMBL-3 Balb/c mouse genomic library. The gene encoding loricrin was located within two Bam HI fragments of 3.4 and 3.1 kb. The coding sequence within this genomic fragment is identical to the cDNA sequences and is not interrupted by introns. There is, however, an intron in the 5' non-coding region that is approximately 1.1 kb in length. In addition to the intron and coding sequence, there is approximately 1.5 kb of 5' flanking sequence and 2.1 kb of 3' flanking sequence.

Construction and Characterization of a Vector from the Loricrin Gene

Figure 1:
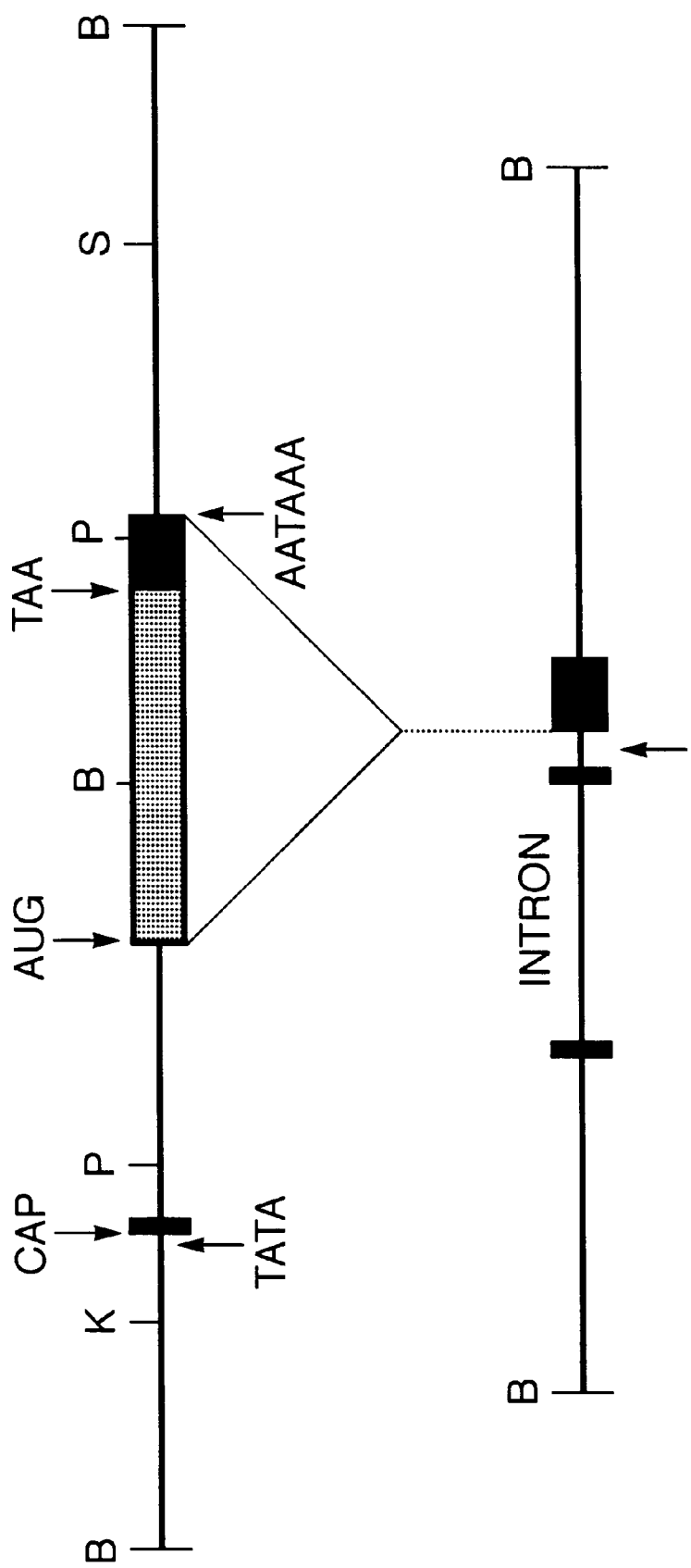
FIG. 1 is a schematic drawing of the mouse loricrin gene and the epidermal vector derived from the loricrin regulatory sequences.

In order to incorporate into a vector the regulatory elements of the loricrin gene, a vector with 5' and 3' flanking regions of the isolated loricrin gene was designed as follows. Polymerase chain reaction (PCR) technology was used to delete the loricrin coding region, leaving the 5' and 3' flanking regions, 5' and 3' non-coding regions and the intron (FIG. 1). A unique Cla I restriction site was engineered at the start (ATG) and stop (TAA) codons to allow easy insertion of exogenous gene cassettes.

The sequence for the loricrin gene which is used for preparing the loricrin constitutive vector is shown in Sequence ID No. 1. The following is but one example of the sequences used from the loricrin gene to construct the constitutive vector. This is not intended to be limiting. The loricrin constitutive vector has a 5' flanking region comprising nucleotides 1 to 1540 of Sequence ID No. 1; an intron and intron/exon boundary comprising nucleotides 1587 to 2677 of Sequence ID No. 1; a 3' flanking region comprising nucleotides 4384 to 6530 of Sequence ID No. 1; and a linker to be inserted at the unique Cla I site at nucleotides 2700 to 2705 of Sequence ID No. 2. The loricrin constitutive vector has a 5' flanking region of approximately 1.5 kb, an intron of approximately 1.1 kb and a 3' flanking sequence of approximately 2.1 kb. The linker of the loricrin constitutive vector can be a polylinker. The poly-linker includes a plurality of restriction endonuclease sites.

To assess the expression characteristics of this vector, a reporter gene, the bacterial gene encoding chloramphenicol acetyl transferase (CAT), was inserted into the Cla I site. The expression vector was analyzed by transient transfection into primary mouse epidermal cells.

Figure 2:
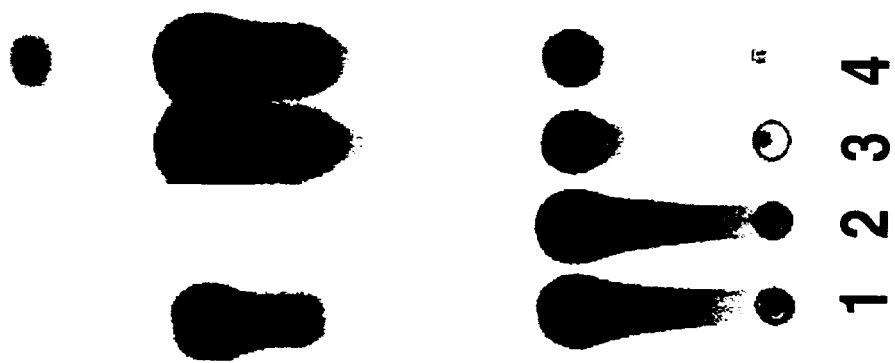
FIG. 2 shows the expression characteristics of the epidermal vector with loricrin regulatory sequences in undifferentiated and differentiated epidermal cells utilizing a reporter gene encoding chloramphenicol acetyl transferase (CAT).

Positive (pSV2.CAT, lane 1) and negative (pA10.CAT, lane 2) control vectors were included in the assay (FIG. 2). The loricrin expression vector had high activity in undifferentiated (low $Ca^{24}$ medium, lane 3) and differentiated (high $Ca^{24}$ medium, lane 4) epidermal cells, surpassing levels obtained with the strong promoter of the virus SV40. This result was unexpected, since previous in vivo studies had demonstrated that the loricrin gene was only expressed at a late stage of epidermal differentiation (Mehrel, et al., Cell, Vol. 61, pp. 1103–1112 (1990)), and indicates that additional flanking sequences are required to suppress loricrin expression in undifferentiated epidermal cells.

To analyze the expression characteristics of the loricrin vector in vivo, the bacterial gene encoding β-galactosidase was inserted into the Cla I site. The β-galactosidase gene has frequently been used as a reporter gene to assess targeting specificity (MacGregor, et al., In: Methods in Molecular Biology, Vol. 7, pp. 217–235 (1991)). This construct was designated pML-β-gal and was used in the production of transgenic mice.

This construct was digested with Apa I and subjected to preparative agarose gel electrophoresis to purify the pML-β-gal expression construct away from plasmid sequences (PGEM72) which might interfere with expression. The separated expression construct sequences were purified and recovered using NA 45 DEAE membrane (Schleicher & Schuell). DNA was precipitated and resuspended at 1–3 ng/μl. ICR outbred female mice (Sasco) were given PMS and HCG to stimulate superovulation, mated to FVB males (Taconic) and resulting one-cell fertilized embryos were collected from the oviducts. DNA was micro-injected into the pronuclei and the embryos were surgically transferred to pseudopregnant recipient females (the result of mating ICR females with vasectomized $B_6D_2F_1$ males (Taconic). Normal gestation and birth was allowed to continue and at approximately three weeks of age the pups were screened for evidence of the transgene using total genomic DNA extracted from the tail.

PCR analysis was performed on the extracted tail using oligo primers specific for β-galactosidase. Animals positive for the transgene were further analyzed to assess the expression characteristics of pML-β-gal. This was done by removing part of the ear and incubating the tissue in a staining solution containing X-gal. Typical results are where a PCR positive animal expressed high levels of β-galactosidase in the epidermis while a PCR negative animal shows no such staining indicating that endogenous murine β-galactosidase is not expressed at sufficient levels in the epidermis to cause false positives in this assay. Intense X-gal staining was detected in the basal compartment as well as the suprabasal, more differentiated layers.

β-gal expression was observed in the epidermis, oral mucosa, esophagus, forestomach, tongue and estrogen-stimulated vaginal epithelium of the transgenic mice but not in the uterus, liver, kidney, and spleen. These results show that the loricrin expression vector contains regulatory sequences required to direct tissue-specific expression.

The data above indicates that the expression vector with loricrin regulatory sequences is useful as a vector to direct the efficient expression of exogenous DNA in both the undifferentiated and differentiated compartments of the epidermis. In addition, the vector directs tissue-specific expression to the epidermis but inappropriate expression with respect to differentiation state.

Characterization of the Loricrin 5' and 3° Flanking Regions

In order to determine regulatory elements and elements responsible for the differentiation-specific expression deletions were made to the loricrin gene 5' and 3' flanking regions in the expression vector. To identify additional 5' and 3' flanking sequences required for differentiation-specific expression, a genomic clone that contains 6.4 kb of additional 5' flanking sequence and 0.5 kb of additional 3' flanking sequence was isolated. These sequences were inserted onto the 5' and 3' ends of pML.β-gal and the construct was assessed in transgenic mice for differentiation-specific expression.

Figure 8A:
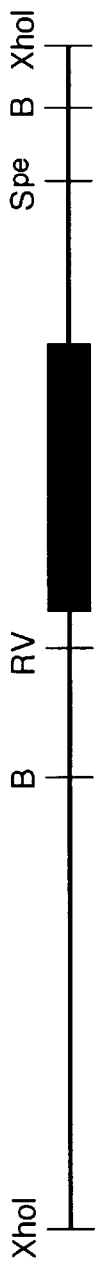
FIGS. 8A–C is a schematic drawing of epidermal vectors with additional 5' and 3' flanking sequences of the loricrin regulatory sequences.
Figure 8B:
Figure 8C:
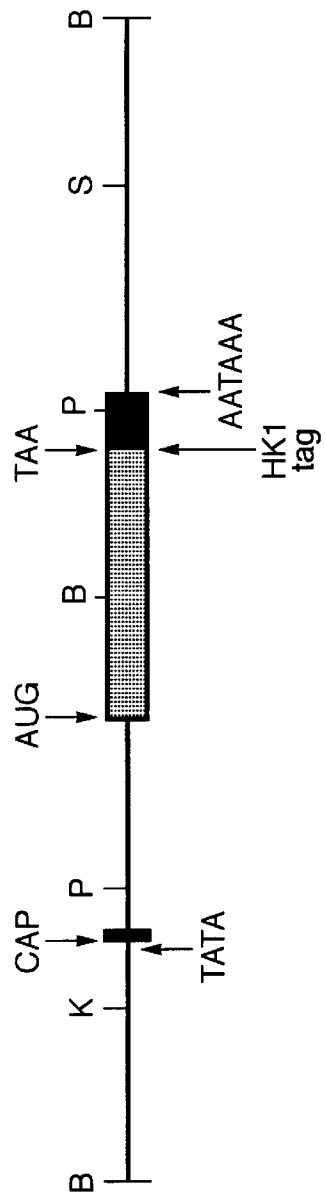
Figure 9:
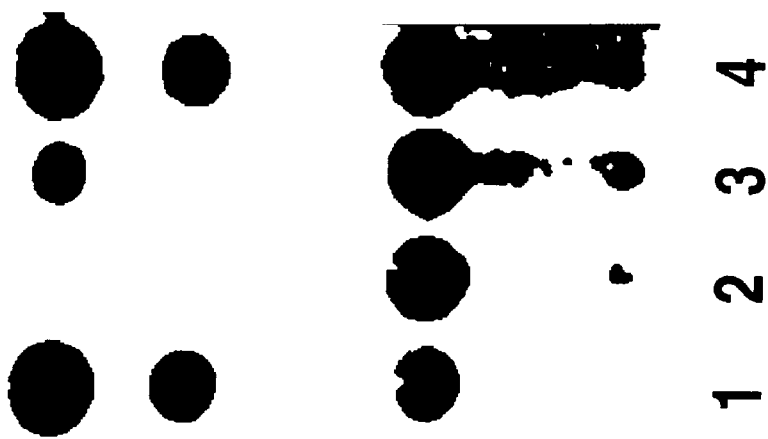
FIG. 9 shows expression characteristics in keratinocytes of epidermal vectors derived from additional 5' and 3' flanking sequences of the loricrin regulatory sequences.

To initially assess the expression characteristics of the genomic clone that contained 6.4 kb of additional 5' flanking sequence and 0.5 kb of additional 3' flanking sequence, a reporter construct pML.14 CAT by inserting the EcoRV-Spe I fragment from pML.6.5 CAT (FIG. 8) was constructed. pML.6.5 CAT is the loricrin expression vector described above (pML.β-gal), but containing the reporter gene encoding chloramphenicol acetyl transferase (CAT). Both constructs were transfected into primary mouse epidermal cells and assayed under proliferating (low $Ca^{++}$) and differentiating (high $Ca^{++}$) conditions. pML.14 CAT exhibited 4.7 times more activity in differentiated cells as compared to proliferating cells (FIG. 9), whereas pML.6.5 CAT was only 1.7 times more active in differentiated cells due to the high activity in proliferating cells.

The in vitro results shows that pML.14 contains additional regulatory sequences that preferentially directs expression in differentiated cells. To assess this in vivo, an epitope tag (derived from the C-terminal sequence of the human keratin 1 protein was asserted as part of the C-terminal sequence of mouse loricrin. This construct is designated pML.6.5.HK1 in FIG. 10. The epitope tagged loricrin coding sequence was then transferred into pML.14 via unique EcoRV and Spe I sites. Eight founder mice which contain the pML.14 HK1 transgene were generated. Founder mice were mated and the F1 mice analyzed for appropriate expression by double-label immunofluorescence with rabbit anti-sera specific for loricrin and guinea pig antibodies specific for the HK1 epitope. Expression was directed differentially.

Figure 10:
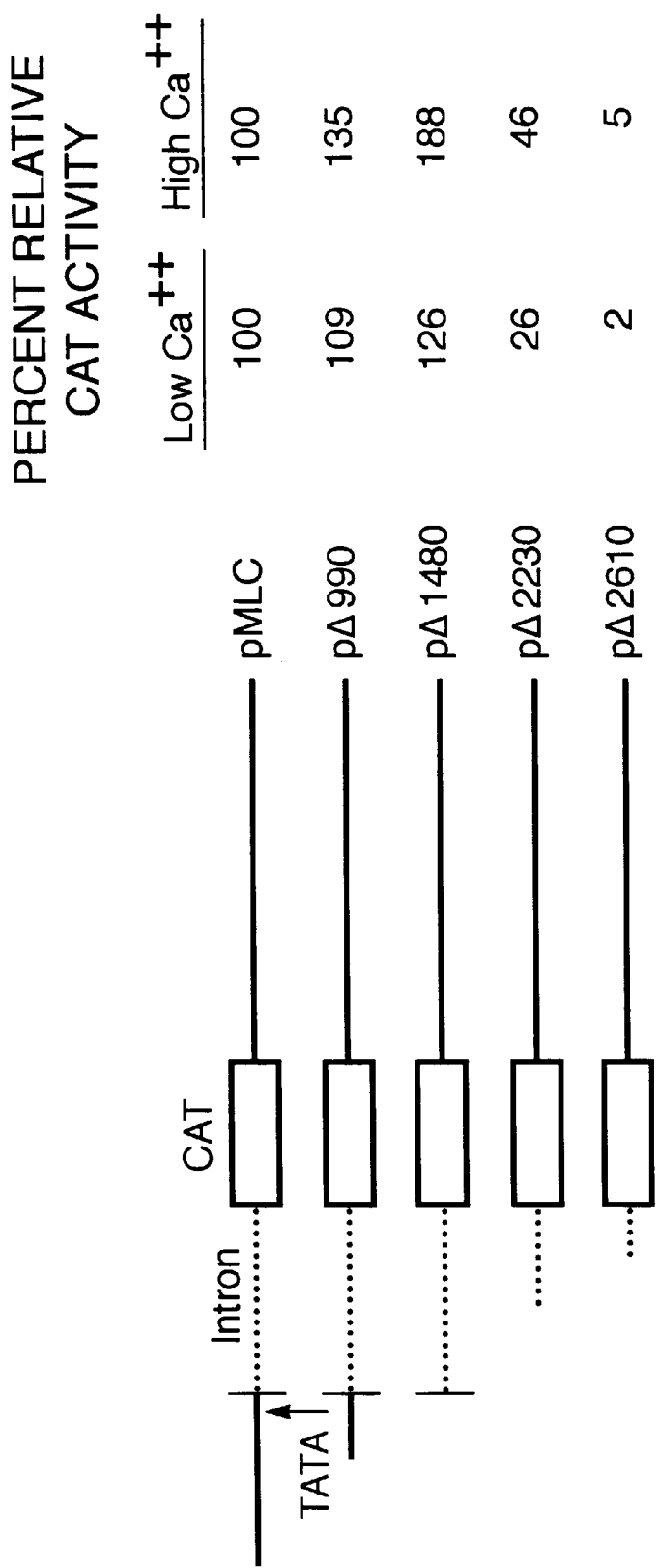
FIG. 10 demonstrates expression characteristics of vectors with 5' deletions of the loricrin regulatory sequences.
Figure 11:
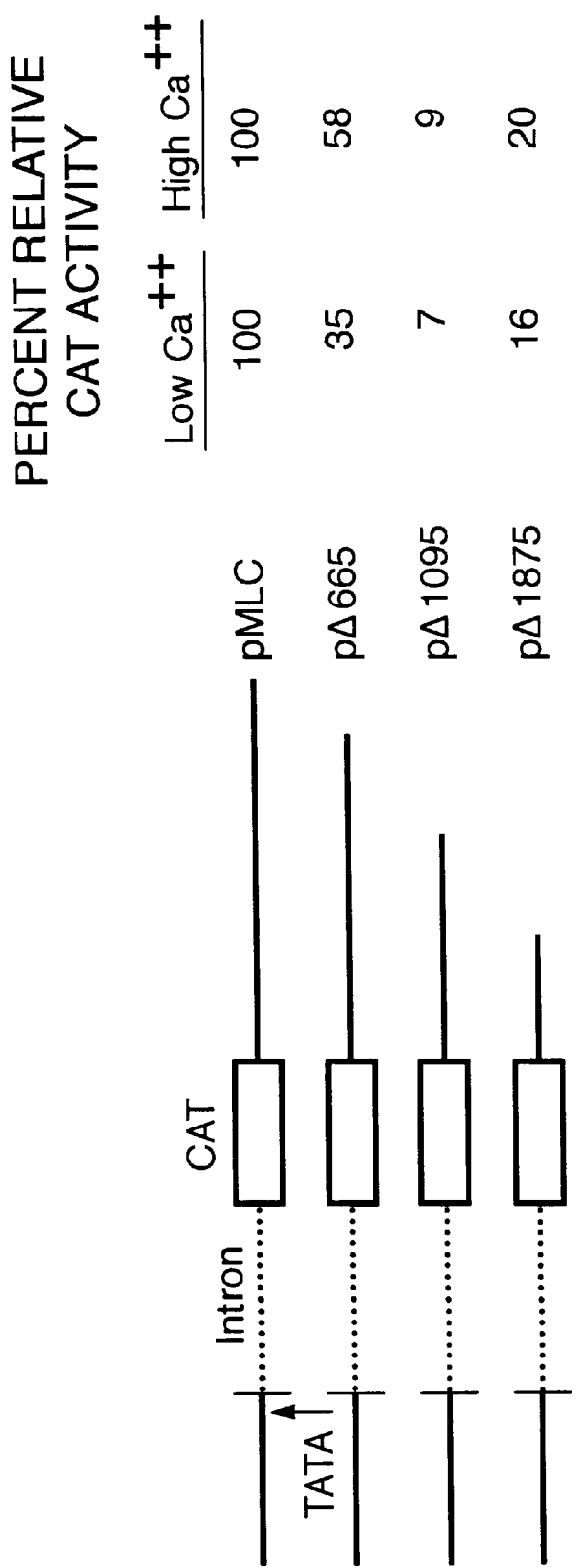
FIG. 11 demonstrates expression characteristics of vectors with 3' deletions of the loricrin regulatory sequences.

Since pML.6.5 demonstrated high activity in undifferentiated epidermal cells (both in vitro and in vivo) and it exhibits tissue and developmental-specific expression, a series of deletion constructs to localize the regulatory elements responsible for these activities were produced. The deletion constructs, shown schematically in FIG. 10 were also analyzed. FIG. 10 summarizes results obtained with the 5' deletions. Sequences between approximately −1 and −500 bp are necessary but not sufficient for CAT expression. Construct pΔ2230, in which the TATA box was deleted, retained some CAT activity. Recent data obtained by a 5' RACE-PCR approach and sequence analysis identified a CAAT box, TATA box and CAP site within the intron, thus explaining this observation. FIG. 11 summarizes results obtained with the 3' deletions. Two regions were identified with potential regulatory sequences. The region deleted in pΔ665 and the region deleted in pΔ1095. The results show that both 5' and 3' regulatory sequences are required for efficient expression of the loricrin expression construct in primary epidermal cells. The deletion studies allowed determination of the approximate location of these sequences. The precise location and identity of these elements can be determined by DNase I footprinting and band shift assays, techniques well known in the art.

To assess the effects of premature expression of loricrin in the basal and spinous layers of the epidermis, the expression characteristics of pML.6.5 was exploited. As discussed above, the pML.6.5 vector directed inappropriate expression of the β-gal reporter gene in the basal and spinous cells of transgenic mice. Therefore, the pML.6.5 HK1 construct shown in FIG. 8 to generate transgenic mice was used. The F1 progeny of the transgenic mice were analyzed for expression at the protein level using HK1 epitope-specific antisera. No phenotypic effects from premature expression of loricrin were observed.

A 6.5 kbp genomic fragment containing the entire loricrin gene was isolated, including 1.5 kbp of 5' flanking sequences and 2.1 kbp of 3' flanking sequences. To further identify elements regulating expression of the mouse loricrin gene, the 5' and 3' flanking sequences from the genomic fragment were placed into a SV40 minimal promoter CAT (chloramphenicol acetyl transferase) construct. These regions were unable to enhance the SV40 heterologous reporter when transfected into primary murine keratinocytes.

To perform this analysis in the context of the homologous promoter, the loricrin coding sequence with the CAT reporter gene was replaced. This construct, pML.CAT, showed high CAT expression in transfected murine primary keratinocytes cultured under undifferentiated (low $Ca^{2+}$) and differentiated (high $Ca^{2+}$) conditions. A similar construct, pML.βGAL, containing beta-galactosidase as the reporter, was used in transgenic mouse studies. High levels of beta-galactosidase expression were observed throughout the epidermis, including the basal cell layer, thus confirming the in vitro observations. A 400 bp fragment within the 3' flanking region is also required for efficient CAT expression. These data suggest that additional elements, located outside the 6.5 kbp fragment are required to restrict expression of the loricrin gene to the granular layer. Taken together, these results suggest that both 5' and 3' regulatory elements are required for efficient expression of loricrin in basal cells.

Vitamin D1 Responsive Element

It has been found that the vectors with loricrin regulatory sequences can be further regulated by introducing the Vitamin $D_3$ regulatory element into the vector. The Vitamin $D_3$ regulatory element is usually introduced into the 3' flanking sequence. In the present invention, the Vitamin $D_3$ regulatory element is from the human K1 keratin gene. With the Vitamin $D_3$ regulatory element in the vector, the expression of the nucleic acid cassettes can be suppressed by Vitamin D, a commonly used substance in animals and humans.

This example demonstrates that a negative regulatory element from the human K1 keratin gene (HK1.NRE) is able to suppress a heterologous promoter in response to Vitamin $D_3$. The HK1.NRE is 70 nucleotides in length (see FIG. 3). PCR technology was used to generate Bam HI and Bgl II sites at opposite ends of this fragment. This facilitates generating multiple copies of this fragment since ligation and digestion with Bam HI and Bgl II will select for oligomers which have ligated head to tail. Four tandem copies of the HK1.NRE were inserted into the Bgl II cloning site of pΔ10.CAT.

Figure 3:
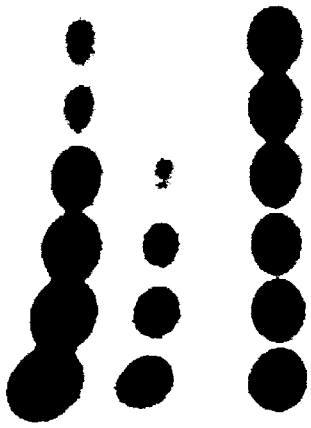
FIG. 3 demonstrates the suppression by Vitamin $D_3$ of a novel negative regulatory element from the human K1 keratin gene (HK1.NRE).
Figure 4:
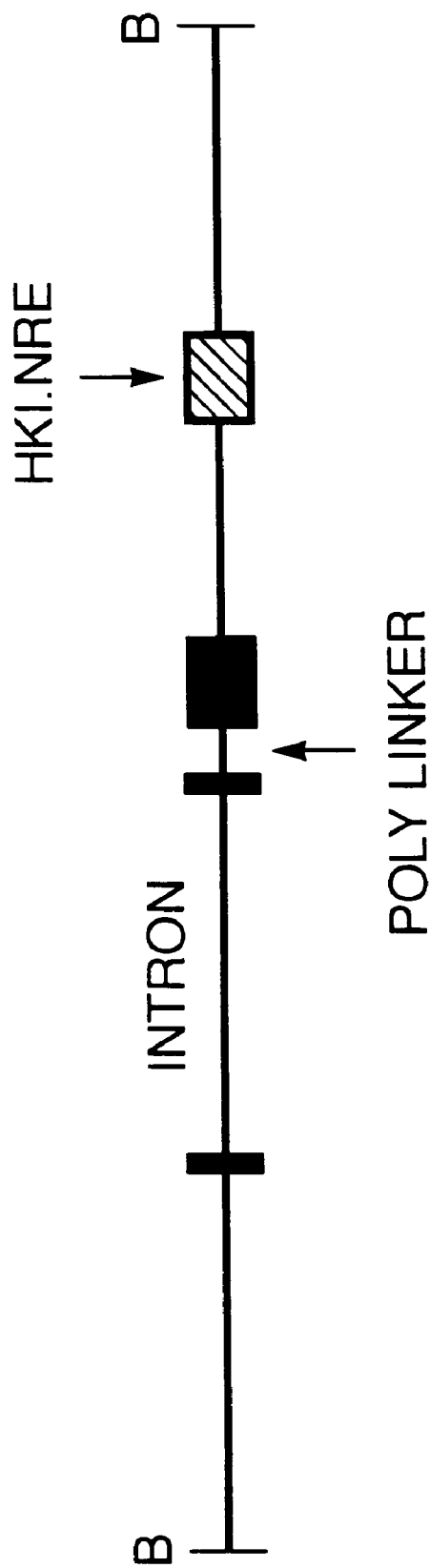
FIG. 4 is a schematic representative of the epidermal vector with loricrin regulatory sequences which can be suppressed by Vitamin $D_3$ via insertion of the HK1.NRE.

In the absence of Vitamin $D_3$ this construct is highly expressed when transfected into primary mouse epidermal cells (FIG. 3). The addition of increasing concentrations of Vitamin $D_3$ to the culture medium completely suppresses transcription of this heterologous promoter. Thus, by using Vitamin $D_3$, the activity of the expression vector is modulated. FIG. 4 shows a schematic representative of a derivative of the loricrin constitutive epidermal vector which contains the HK1.NRE in its 3' flanking region. The activity of this vector within epidermal cells can be suppressed by topical application of Vitamin $D_3$, or an analogue, to the skin. In addition, it has been shown that activity of this vector can be restored with retinoic acid.

EXAMPLE 2

Mouse K6 Keratin Gene

Several laboratories have reported that keratin K6 is not expressed in normal epidermis, but is expressed under hyperproliferative conditions such as wounding (Weiss, et al., J. Cell Biol., Vol. 98, pp. 1397–1406 (1984); Nakazawa, et al., J. Cell Biol., Vol. 103, pp. 561a (1986); Stoler, et al., J. Cell Biol., Vol. 107, pp. 427–446 (1988)) or topical application of retinoic acid (Rosenthal, et al., J. Invest. Dermatol., Vol. 95, pp. 510–515 (1990). Although K6 expression does not occur in interfollicular epidermis, it does occur in hair follicles (Nakazawa, et al., J. Cell Biol., Vol. 103, pp. 561a (1986)).

Recent results indicate that there are two K6 cDNAs that differ in sequence in only a few nucleotides (denoted mk6a and mk6b). These cDNA clones have been used to differentially screen a EMBL 3 Balb/c mouse genomic library and isolate two distinct K6 genes. These genes are closely linked within genomic DNA, i.e., arranged in tandem. They are separated by 10.5 kb of intergenic sequences. They have almost identical 3' halves, including identical 3' non-coding and flanking regions. Interestingly, the 5' halves of the two genes differ greatly in their restriction fragment patterns.

Sequence analysis of the region near the ATG shows many differences between the two genes. Sequence analysis of these two genes revealed that they encode essentially the same protein product with the amino acid differences (13 out of 554 residues) being mostly conservative. This identity of sequence precludes an immunochemical approach in identifying the two gene products, however both the 5' and 3' non-coding sequences show some divergence. These differences were exploited to generate specific oligos to each and by RT-PCR both genes were shown to be transcriptionally active. Although the coding sequences for these two genes are essentially the same, the promoter regions show remarkably little identity.

The sequence of one of these genes, designated BCM-MK6(A), is shown in Sequence ID No. 3. To determine the expression characteristics of this gene in vivo in transgenic mice, PCR technology was used to modify a 13.5 kb Xho I fragment containing BCM-MK6 (A). Nucleotides encoding the C-terminal region of the K6 protein were deleted and nucleotides encoding the amino acid sequence Sequence ID No. 4 were inserted. These amino acids are at the C-terminal of human keratin K1 (Johnson, et al., PNAS, USA, Vol. 82, pp. 1896–1900 (1985)). A schematic representative of this derivative of the mouse K6 gene (BCM-MK6(A)-HK1) is shown in FIG. 5.

Antisera have previously been generated against the HK1 C-terminal peptide (Rosenthal, et al., J. Invest. Dermatol., Vol. 95, pp. 510–515 (1990)). These antibodies are monospecific for this human K1 peptide and allow expression of the derivatized BCM-MK6(A)-HK1 transgene to be followed against the expression pattern of the endogenous mouse K6 genes.

Figure 5:
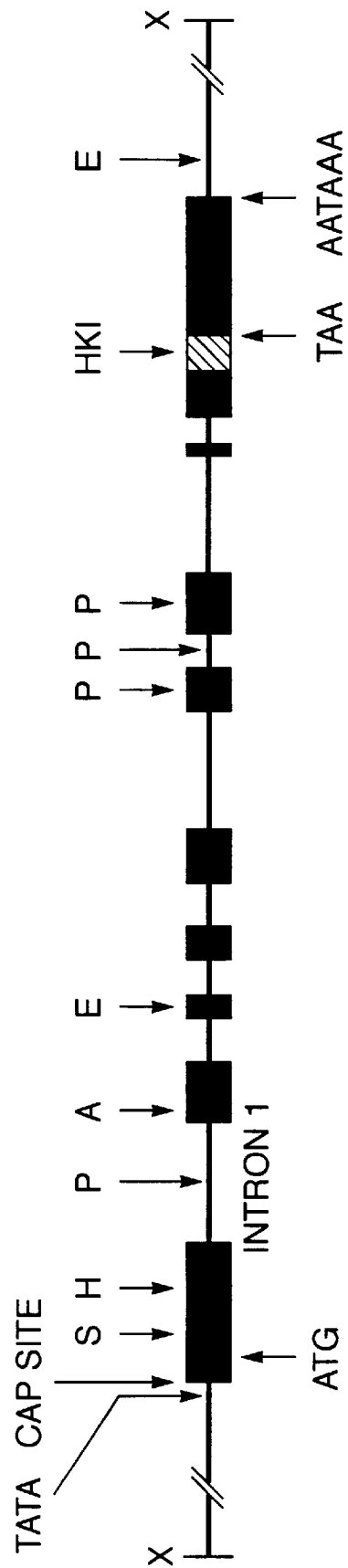
FIG. 5 is a schematic drawing of a derivative of the mouse K6 keratin gene (BCM-MK6(A)-HK1).

The derivatized mouse K6 transgene shown in FIG. 5 was used in the production of transgenic mice as outlined above. Mice resulting from the initial injections were screened by PCR analysis for presence of the BCM-MK6(A)-HK1 transgene. Positive founders were initially analyzed for transgene expression as follows. A small ear biopsy was taken and after 48 hours a second biopsy was taken at the same site to score for expression during wound healing. Transgene expression was limited to hair follicles in the initial biopsy and was inducible in interfollicular epidermis. In fact, the MK6a transgene could account for most of the observed expression of K6. Some differential expression was seen in the tongue but the significance of this is not known. Transgene expression was observed in the epidermis in the 48 hour biopsies, but only at the site of wounding.

To further confirm the inducibility of the BCM-MK6(A)-HK1 transgene under hyperproliferative conditions, F1 generation offspring from the initial founders were treated topically with the hyperplasiogenic agent 12-O-tetradecanoylphorbol-13-acetate. Biopsies were taken before and 48 hours after topical application of this agent. Immunofluorescence was performed on frozen sections of these biopsies with antisera specific for the HK1 peptide. No expression was observed prior to the induction of hyperplasia, however, the BCM-MK6(A)-HK1 protein was expressed at very high levels in all layers of the epidermis 48 hours after hyperplasia was induced.

Construction of an Epidermal Expression Vector from the Mouse K6 Gene (BCM-MK6(A)

Results obtained with the derivative of BCM-MK6(A) indicate that all of the regulatory sequences required to suppress expression of this gene in normal epidermis and activate its expression under hyperproliferative conditions, such as in wounding healing or experimentally induced hyperplasia, are located within the 13.5 kb Xho I fragment (FIG. 5). Therefore, a vector was developed from this fragment.

This vector is very useful in gene therapy applications where dosage of pharmaceuticals needs to be regulated. In addition, this vector is ideally suited for wound healing applications since it is induced during the wound healing process but suppressed after healing has occurred. This example is not meant to limit the present invention in any manner.

Figure 6:
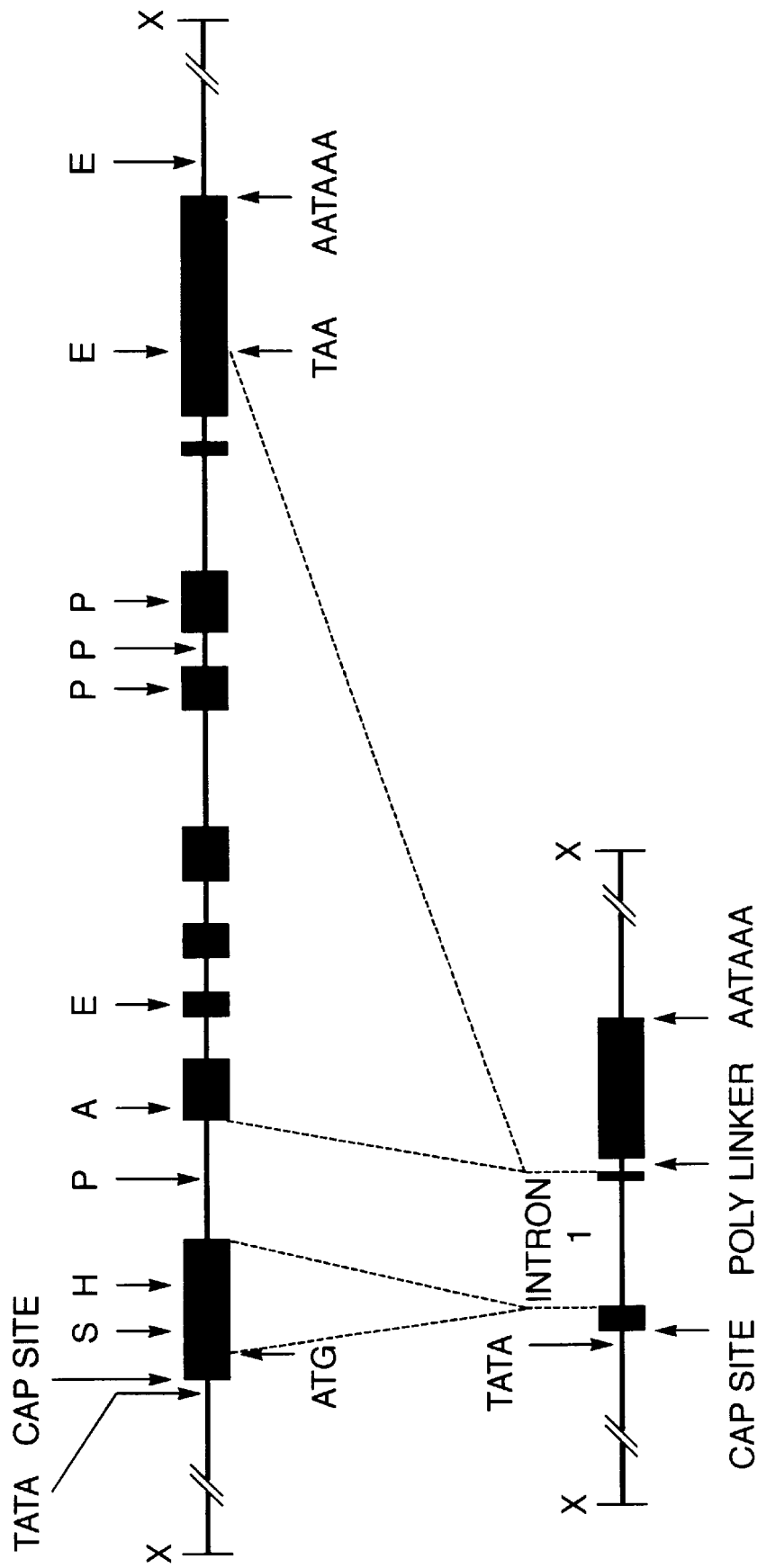
FIG. 6 is a schematic drawing of the mouse K6 keratin gene and the proposed construction of an epidermal vector with K6 keratin regulatory sequences.

FIG. 6 illustrates how a vector is constructed from the BCM-MK6(A) gene. The vector is derived from the 13.5 kb Xho I fragment which contains the entire K6 gene. The same general strategy used in construction of the epidermal vector with the loricrin regulatory sequences (FIG. 1) is followed.

The expression vector retains all of the 5' flanking sequences, the 5' non-coding sequences up to but not including the ATG, the first intron including the splice-sites of the intron-exon boundary and all of the 3' non-coding and flanking sequences after the TAA codon. A polylinker is engineered 3' of the first intron to allow easy insertion of exogenous DNA cassettes. These manipulations are performed through the use of PCR technology. Unique Xho I sites are conserved at the ends of the vector to allow easy amplification in pGEM vectors and excision for purification from plasmid sequences.

In vivo results indicate that the endogenous human K6 gene is inducible after topical application of all-trans retinoic acid. Further, in vivo mouse experiments indicate that the vector shown in FIG. 6 is inducible by topical application of retinoic acid, or an analogue, to the skin.

The partial sequence for the K6 keratin gene which is used for preparing the K6 keratin vector is shown in schematic form in FIG. 6 and the sequence is shown in Sequence ID No. 3. The K6 keratin vector has a 5' flanking region which extends from a unique 5' Xho I site up to nucleotide 360 of SEQ. ID. No. 3; an intron and intron/exon boundary comprising nucleotides 928 to 1494 of SEQ. ID. No. 3; a 3' flanking region which extends from nucleotide 4740 of SEQ. ID. No. 3 to a unique 3' Xho I site; and a poly linker inserted between nucleotides 1504 to 1509 of SEQ. ID. No. 3.

The keratin K6 inducible vector has a 5' flanking region of approximately 8.0 kb, an intron and intron/exon boundary of approximately 0.56 kb and a 3' flanking sequence of approximately 1.2 kb. The restriction endonuclease sites found in the linker and poly-linker of the loricrin and keratin K6 vectors can be any restriction endonucleases which will allow insertion of the nucleic acid cassette. In the preferred embodiment they are usually selected from the group consisting of Cla I, Not I, Xma I, Bgl II, Pac I, Xho I Nhe I and Sfi I.

Characterization of the K6 5' and 3° Flanking Regions

Keratin K6 is normally expressed in the hair follicle and under hyperproliferative conditions such as is seen in wounding or when keratinocytes are grown in culture. Given the unique expression characteristics of this protein, and the results obtained with the derivative of BCM-MK6(A) indicating that regulatory sequences required to suppress expression of this gene in normal epidermis and activate its expression under hyperproliferative conditions were present, the K6 gene 5' and 3' flanking regions were analyzed for promoter and regulatory sequences.

In an attempt to identify these sequences, transgenic mice with a 13.5 kbp fragment encoding the mouse K6 gene were produced. This fragment contains a complete K6 gene with 7.7 kbp of 5' flanking and 1.5 kbp of 3' flanking sequences.

The c-terminal of the K6 protein was replaced with the c-terminal epitope of human K1 to enable co-analysis, by double-label immunofluorescence, of expression of both the K6 transgene and the endogenous K6 gene.

Expression of the K6 transgene paralleled that of the endogenous gene in the periderm during fetal development. Expression was first observed at day 15 and persisted until the periderm was sloughed off at day 19. The K6 transgene was expressed, post-natally, in the same differentiation-compartment of the hair follicle as the endogenous gene.

An analysis of internal tissues showed that the transgene retained the same specificity as the endogenous gene. The transgene was expressed in the cheek pouch, tongue and esophagus but not in the stomach, bladder, liver or spleen. The topical application of TPA (12-O-tetradecanoylphorbol-13-acetate) an agent that produces hyperproliferation of epidermal keratinocytes, induced expression of the transgene in the non-follicular epidermis of these mice. K6 transgene expression was also induced by the topical application of retinoic acid and the kinetics of induction were the same as the endogenous gene.

Additionally, keratinocytes harvested from these mice expressed the transgene when grown in culture. These studies established that the 13.5 kbp transgene contains all the cis regulatory elements required for correct expression of K6.

Vitamin $D_3$ Responsive Element

Figure 7:
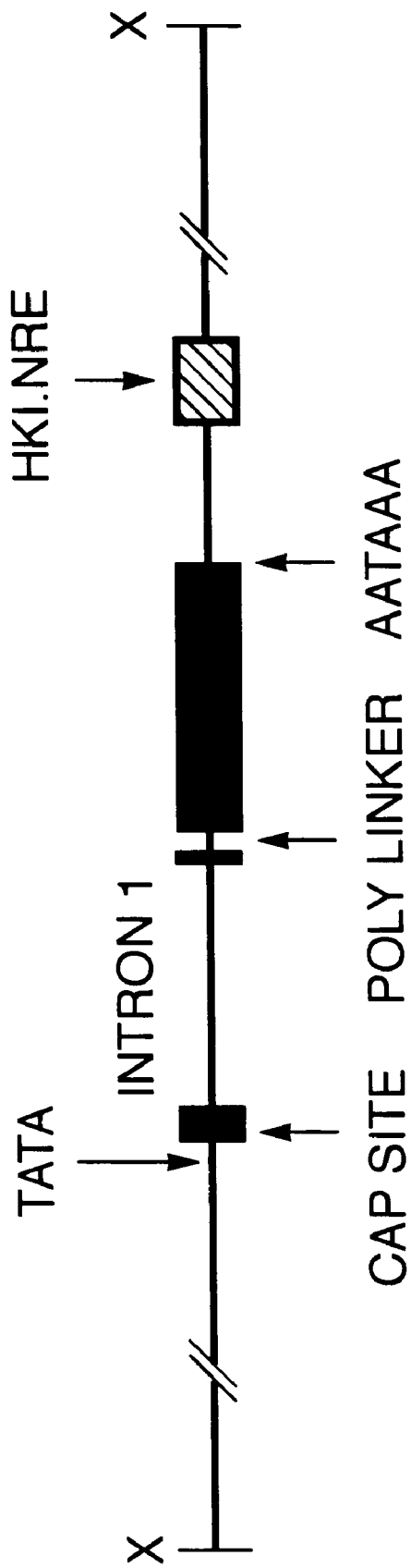
FIG. 7 is a schematic representative of the epidermal vector with K6 keratin regulatory sequences which can be suppressed by Vitamin $D_3$ via insertion of HK1.NRE.

Even though the inducible epidermal vector depicted in FIG. 6 is suppressed or silent in normal epidermis, it can be accidently induced as a result of injury. Therefore, it is desirable to have an additional suppressor engineered into this construct. In addition, this suppressor is used to more tightly regulate pharmaceutical delivery. This is achieved by insertion of the HK1.NRE described in FIG. 3 and discussed above. FIG. 7 shows a schematic representative of a derivative of the K6 epidermal vector which contains the HK1.NRE in its 3' flanking region. The activity of this vector within epidermal cells is suppressed by topical application of Vitamin $D_3$, or an analogue, to the skin. It is restored with the topical application of retinoic acid or an analogue to the skin.

Cell Transformation

One embodiment of the present invention includes cells transformed with the vectors described above, i.e. to transformed epidermal cells with vectors containing loricrin or K6 keratin regulatory sequences. Once the epidermal cells are transformed, the epidermal cells will express the protein, polypeptide or RNA encoded for by the nucleic acid cassette. This is not intended to be limiting in any manner.

The nucleic acid cassette which contains the genetic material of interest is positionally and sequentially oriented within the vectors such that the nucleic acid in the cassette can be transcribed into RNA and, when necessary, be translated into proteins or polypeptides in the transformed epidermal cells. A variety of proteins and polypeptides can be expressed by the sequence in the nucleic acid cassette in the transformed epidermal cells. These proteins or polypeptides which can be expressed include hormones, growth factors, enzymes, clotting factors, apolipoproteins, receptors, drugs, tumor antigens, viral antigens, parasitic antigens and bacterial antigens. Specific examples of these compounds include proinsulin, insulin, growth hormone, androgen receptors, insulin-like growth factor I, insulin-like growth factor II, insulin growth factor binding protein, epidermal growth factor TGF-α, dermal growth factor PDGF, angiogenesis factors, e.g., acid fibroblast growth factor, acidic and basic fibroblast growth factor and angiogenin for instance, matrix proteins such as Type IV collagen, Type VII collagen, laminin and proteins from viral, bacterial and parasitic organisms which can be used to induce immunologic response.

Transformation can be done either by in vivo or ex vivo techniques. One skilled in the art will be familiar with such techniques for transformation. Transformation by ex vivo techniques includes co-transfecting the epidermal cells with a vector containing a selectable marker. This selectable marker is used to select those cells which have become transformed. Selectable markers are well known to those who are skilled in the art.

For example, keratinocytes can be serially propagated in culture. The vectors can be administered to the cells by the methods discussed below. The transformed cell can then be lifted from the culture and used for skin grafting.

Administration

Administration as used herein refers to the route of introduction of a vector or carrier of DNA into the body. Administration may include intravenous, intramuscular, topical, or oral methods of delivery. Administration can be directly to a target tissue or through systemic delivery.

In particular, the present invention can be used for treating disease or for administering the loricrin or K6 vectors capable of expressing any specific nucleic acid sequence in epidermal tissue. Administration can also include administering a regulatable vector discussed above. Such administration of a vector can be used to treat disease. This can include a variety of methods of administration such as direct gene transfer in to skin tissue by liposomes, proteoliposomes, calcium phosphate-coprecipitated DNA, DNA coupled to macromolecular complexes, DNA transporters, DNA coated microprojectiles, coated plasmids, direct microinjection, hypospray, as well as use of skin grafts.

In particular, gene transfer using the above mentioned vectors can be administered by direct microinjection, electroporation, liposomes, proteoliposomes, calcium phosphate-coprecipitation, skin grafts, retroviral vectors, DNA coupled to macromolecular complexes, DNA transporters and microprojectiles. Routes of administration include intramuscular, aerosol, oral, topical, systemic, ocular, intraperitoneal and/or intrathecal.

The special delivery route of any selected vector construct will depend on the particular use for the loricrin or K6 keratin vectors. In general, a specific delivery program for each vector construct used will focus on vector uptake with regard to the particular targeted tissue, followed by demonstration of efficacy. Uptake studies will include uptake assays to evaluate cellular uptake of the vectors and expression of the tissue specific DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

DNA uptake by keratinocytes have the unique ability to take up DNA from the extracellular space after simple injection of concentrated DNA solutions into the skin. Expression of DNA by this method can be sustained for several months.

Incorporating DNA into macromolecular complexes that undergo endocytosis increases the range of cell types that will take up foreign genes form the extracellular space. Such complexes may include lipids, polylysine, viral particles, ligands for specific cell-surface receptors or nuclear proteins. Lipid-DNA complexes could be useful for introducing into the skin for delivery of transgenes into the keratinocytes of intact animals.

Administration of DNA-coated microprojectiles by a gene gun requires instrumentation but is as simple as direct injection of DNA. A construct bearing the gene of interest is precipitated onto the surface of microscopic metal beads. The microprojectiles are accelerated with a shock wave or expanding helium gas, and penetrated tissues to a depth of several cell layers. This approach permits the delivery of foreign genes to the skin of anesthetized animals. This method of administration achieves expression of transgenes at high levels for several days and at detectable levels for several weeks. This is the preferred method of administration.

Administration can also be through use of DNA transporters. DNA transporters refers to molecules which bind to DNA vectors and are capable of being taken up by epidermal cells. DNA transporters contain a molecular complex capable of non-covalently binding to DNA and efficiently transporting the DNA through the cell membrane. It is preferable that the transporter also transport the DNA through the nuclear membrane.

In a preferred method of administration involving a DNA transporter system, the DNA transporter system has DNA binding complex with a binding molecule capable of non-covalently binding to DNA which is covalently linked to a surface ligand. The surface ligand is capable of binding to a cell surface receptor. In addition, a second DNA binding complex is capable of non-covalently binding to DNA and is covalently linked to a nuclear ligand. The nuclear ligand is capable of recognizing and transporting a transporter system through a nuclear membrane. Additionally, a third DNA binding complex may be used which is also capable of non-covalently binding to DNA. The third binding molecule covalently linked to a virus. The binding molecules can be spermine, spermine derivative, histones, cationic peptides and/or polylysine.

Gene delivery can also be administered by using human epidermal keratinocytes. These cells are uniquely suitable for engraftment. Large numbers of cells can be generated by cultivation of a small biopsy. The cultures can be prepared as stratified sheets and when grafted to humans, generate epidermis which continues to improve in histotypic quality over many years. The keratinocytes are genetically engineered while in culture by transforming the keratinocytes with the appropriate vector. Although keratinocytes are separated from the circulation by the basement membrane dividing the epidermis from the dermis. Human keratinocytes secret into circulation the protein produced.

Transfer of genes directly has been very effective. Experiments show that administration by direct injection of DNA into skin results in expression of the gene in the area of injection. Injection of human growth hormone gene results in expression of the gene for months at relatively constant levels. The injected DNA appears to persist in an unintegrated extrachromosomal state.

Administration may also be by liposomes. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active.

For example, a liposome delivery vehicle originally designed as a research tool, Lipofectin, has been shown to deliver intact mRNA molecules to cells yielding production of the corresponding protein.

Liposomes offer several advantages: They are nontoxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Topical administration of the vectors is advantageous since it allows localized concentration at the site of administration with minimal systemic adsorption. This simplifies the delivery strategy of the vectors to the disease site and reduces the extent of toxicological characterization. Furthermore, the amount of material to be applied could be potentially small. Effective delivery requires the vector to diffuse into the infected cells. Chemical modification of the vector to help diffusion may be required for penetration, such as permeability enhancers in a liposome.

The chosen method of delivery should result in cytoplasmic accumulation and optimal dosing. The dosage will depend upon the disease and the route of administration but should be between 1–1000 mg/kg of body weight/day. This level is readily determinable by standard methods. It could be more or less depending on the optimal dosing. The duration of treatment will extend through the course of the disease symptoms, possibly continuously. The number of doses will depend upon disease delivery vehicle and efficacy data from clinical trials.

Establishment of therapeutic levels of ribosomes within the cell is dependent upon the rate of uptake and degradation. Decreasing the degree of degradation will prolong the intracellular half-life of the ribosome.

EXAMPLE 3

Methods of Use

The following are methods for using the vectors discussed above. These are offered by way of illustration and not intended to limit the invention in any manner.

Treatment of Wounds or Surgical Incisions

Greater than 3.5 million individuals develop skin ulcers. During normal healing, epidermal cells produce growth factors which affect not only epidermal cells but also cells within the dermis. In addition, epidermal cells synthesize several matrix proteins which provide an anchor to the underlying dermis. Many skin ulcers occur in patients with disorders such as circulatory problems and diabetes, and the normal healing process in impaired. The epidermal vectors are used to target the combined expression of growth factors, to accelerate growth of cells in both the epidermal and dermal compartments; matrix proteins, to increase tensile strength; and angiogenesis factors, to improve circulation, in an attempt to improve healing these patients.

For healing a wound or surgical incision, a vector of this invention maybe introduced in situ. The nucleic acid cassette of the vector will preferably encode a growth factor such as epidermal growth factor, dermal growth factor, transforming growth factor or growth hormone. In vivo transformation can be carried out by known techniques in the art. Administration may be by any of the above-mentioned deliveries.

In one preferred embodiment for the treatment of wounds or surgical incisions, epidermal cells are transformed with a plurality of vectors. In the plurality of vectors, the cassette of at least one vector contains a nucleic acid sequence for an epidermal growth factor (TGF-α), the cassette of at least one vector contains a dermal growth factor (PDGF), a cassette of at least one vector contains a nucleic acid sequence for a matrix protein to anchor the epidermis to the dermis, and a cassette of at least one vector contains a nucleic acid sequence for an angiogenesis factor. The sequence for matrix proteins can be selected from any sequences useful for the anchoring of the epidermis to the dermis but are usually selected from the group consisting of Type IV collagen, laminin, nidogen, and Type VII collagen. The angiogenesis factor is usually selected from the group consisting of acidic fibroblast growth factor, basic fibroblast growth factor and angiogenin.

The combination of the vectors provides all of the necessary elements for quick and rapid enhancement of healing of wounds or surgical incisions. This procedure is very helpful in the case of plastic or reconstructive surgery. Furthermore, skin ulcers can be treated by following similar procedures as described for wound healing or surgical incision. These procedures are useful in animals and humans. Treatment may be administered by any of the techniques discussed above.

In the ex vivo approach for treating or healing wounds, surgical incisions and skin lesions, the vectors are first transformed into the epidermal cells ex vivo. Transformation techniques are well known in the art. The transformed epidermal cells are transplanted onto the animal or human to be treated. The vectors can also be applied directly by anyone of the above mentioned methods of administration.

Treatment of Psoriasis

Psoriasis is a common inherited skin disease which affects approximately 4 million individuals in the U.S., 20 million world-wide. It is characterized by the presence of inflamed scaly skin. Although the specific defect for psoriasis is not known, inappropriate expression of growth factors, and cytokines appears to be responsible for its pathogenesis. Epidermal vectors are used to inhibit the mitogenic effects of positive growth factors produced in psoriatic lesions by expressing negative growth factors which induce growth arrest of epidermal cells.

Thus, one embodiment of the present invention is a method for treating psoriasis. In this method, epidermal cells are transformed in vivo with a loricrin vector or a keratin K6 vector. A nucleic acid cassette in either vector contains a nucleic acid sequence for a protein or polypeptide. The nucleic acid can encode for a TGF-β, a soluble form of a cytokine receptor, and/or an antisense RNA. The nucleic acid may also encode for TGF-β1, a mutant which is constitutively active. Sellheyer, et al. PNAS vol. 90, pp. 5237–5241 (1993). The cytokine receptor is for either IL-1, IL-6 or IL-8 proteins. The antisense RNA sequence can be complementary to mRNA for TGF-α, IL-1, IL-6 and/or IL-8.

The inflammation observed in psoriasis most likely results from inappropriate expression of cytokines. Targeted expression of soluble cytokine receptors prevents stimulation of an inflammatory infiltrate in this disease. In another approach, antisense RNA is directed against transcripts of positive growth factors or cytokines. These approaches have therapeutic potential for other dermatoses resulting from inflammation. Transformation can be done by in vivo or ex vivo techniques. Administration can be by anyone of the above mentioned methods.

Treatment of Cancer

Skin cancer is by far the most common form of cancer with greater than 600,000 new cases reported each year. Several genes have been implicated in causing skin cancer, including loss or mutation of the host cell tumor suppressor gene, p 53 and expression of the E6 and E7 transforming genes of human papilloma virus (HPV). In vitro studies suggest that the normal or wild type p53 gene can revert the phenotype of malignant cells or induce programmed cell death.

In the present invention, the method of treating cancer involves steps of in vivo or ex vivo transformation of epidermal cells with a loricrin vector or a K6 keratin vector. The nucleic acid cassette of either vector contains the nucleic acid sequence coding for antisense RNA for the E6 or E7 gene of the human papilloma virus or coding for the normal p53 protein. Although the example given is for skin cancer, this same approach is used for cancers occurring in other squamous epithelia, since the vectors of this invention will also function in these tissue types.

The epidermal vectors of this invention are used to target expression of the normal p53 gene to cause reversion to a non-malignant phenotype or induction of programmed death in vivo. In cancers where HPV is suspected of being the etiological agent, these vectors are used to target expression of antisense RNA specific for the E6 and E7 genes of HPV. In vivo and ex vivo transformation techniques are known in the art. Administration can be through anyone of the above-mentioned methods.

Treatment of Alopecia

Although the outer root sheath (ORS) is a continuous band of cells surrounding the hair follicle, the cells that make up the ORS differ in their mitotic and migratory activity depending on their position along the follicle. Further, ultrastructural studies have determined two distinct layers in the ORS. Cells adjacent to the base of the papilla give rise to the population of outer root sheath cells that form the innermost layer (companion layer) of ORS cells that move up the follicle adjacent to Henle's layer of the inner root sheath (IRS). Those ORS cells formed above the follicle bulb tend to form a population of cells on the periphery of the ORS.

The companion layer of the ORS is in intimate contact with the cells of the Henle's layer of the IRS. Morphological evidence has shown that these cells of the ORS and IRS form "inter-digitations" between them and that this would allow neighboring cells to migrate up the follicle together. These cells then cornify, degrade and slough into the follicle lumen. Companion cells may play a role in the fate of the IRS and male pattern baldness.

Immunofluorescent data clearly shows K6 expression in the innermost layer of the ORS. Therapeutic approaches using K6 expression vectors can be used for alopecia or male pattern baldness.

To treat alopecia, a K6 expression vector was constructed using the same strategy described above. Exogenous coding sequences in the nucleic acid cassette were inserted at the linker. The nucleic acid encodes for a dominant negative form of the androgen receptor, epimorphin to regenerate new follicles, angiogenesis factors such as TGF-α or acidic and basic fibroblast growth follicle, and antisense or ribozymes against transcripts of 5-α-reductase or an androgen receptor. Transformation of the follicle cells can be performed through known in vivo techniques. Administration can be by any one of the methods discussed above.

Male pattern baldness due to androgen action in the scalp can be treated by reducing the amount of steroid in the scalp. By preventing the metabolism of dihydrotestosterone with antisense 5-α-reductase, the enzyme that metabolizes dihydrotestosterone, the androgen will not initiate trans-activation. This prevents the androgen receptor effects causing alopecia. Likewise, the dominate negative form of the androgen receptor will also prevent trans-activation. In addition, expression of epimorphin will help regenerate hair follicles.

Immune Response

An additional embodiment of the present invention is a method for producing an immunological response. This involves in vivo introduction of the vectors discussed above into epidermal cells. The nucleic acid cassette in the vectors usually codes for a polypeptide which induces an immune response. This includes microbial proteins, viral capsids, bacterial proteins and toxins. An example of this is the viral capsid protein from the human papilloma virus. One skilled in the art will readily recognize that any other variety of proteins can be used to generate a immunologic response and thus produce antibodies for vaccination. In vivo transformation is well known in the art. The transformed epidermal cells can be administered through any of the above mentioned methods.

One skilled in the art will readily appreciate that the present invention is well adapted to carry out the objects and obtain the ends and advantages mentioned, as well as those inherent therein. The transformed epidermal cells, nucleic acid sequences, loricrin vector and K6 keratin vector, along with the methods, procedures, treatments, molecules of specific compounds described herein are presently representative of preferred embodiments, are exemplary and are not intended as limitations on the scope of the invention. Changes therein and other uses will occur to those skilled in the art which are encompassed within the spirit of the invention as defined by the scope of the claims.

It will be readily apparent to one skilled in the art that varying substitutions and modifications may be made to the invention disclosed herein without departing from the scope and spirit of the invention.

All patents and publications mentioned in this specification are indicative of the levels of those skilled in the art to which the invention pertains. All patents and publications which are incorporated herein by reference are incorporated to the same extent as if each individual publication was specifically and individually indicated to be incorporated by reference.

We claim:

1. A vector for expression of a nucleic acid sequence in an epidermal cell, wherein said nucleic acid sequence is other than a mammalian loricrin gene or a mammalian K6 keratin gene, said vector comprising, in operable association:

a 5' flanking region from a mammalian gene including necessary sequences for expression of said nucleic acid sequence;

a 3' flanking region from a mammalian loricrin gene or a mammalian K6 keratin gene which regulates expression predominantly in an epidermal cell of said nucleic acid sequence with which it is associated; and a linker connecting said 5' flanking region to said nucleic sequence, said linker having a position for inserting said nucleic acid sequence, wherein said linker lacks the coding sequences of a gene with which it is naturally associated.

2. The vector of claim 1, wherein said 3' flanking region is 3' to said position for inserting said nucleic acid sequence.

3. The vector of claim 1, wherein said 3' flanking region is 5' to said linker.

4. The vector of claim 1, wherein said vector further comprises a nucleic acid sequence.

5. The vector of claim 1 or 4, wherein said 5' flanking region includes a promoter, a TATA box, a CAP site and a first intron and intron/exon boundary in appropriate relationship for expression of said nucleic acid sequence.

6. The vector of claim 5, wherein said 5' flanking region contains a 5' UTR, and said 3' flanking region contains a 3' UTR and 3' NCR.

7. The vector of claim 1 or 4, wherein said 3' flanking region is from a loricrin gene.

8. The vector of claim 1 or 4, wherein said 5' flanking region and said 3' flanking region are from a loricrin gene.

9. The vector of claim 5, wherein said 5' flanking region is approximately 1.5 kb, said intron and intron/exon boundary is approximately 1.1 kb and said 3' flanking region is approximately 2.1 kb of a loricrin gene.

10. The vector of claim 1 or 4, wherein said 3' flanking region is from a K6 keratin gene.

11. The vector of claim 1 or 4, wherein said 5' flanking region and said 3' flanking region are from a K6 keratin gene.

12. The vector of claim 5, wherein said 5' flanking region is approximately 8.0 kb, said intron and intron/exon boundary is approximately 0.56 kb and said 3' flanking region is approximately 1.2 kb of a K6 keratin gene.

13. The vector of claim 4, wherein said nucleic acid sequence comprises genetic material coding for a protein or a polypeptide.

14. The vector of claim 13, wherein said genetic material codes for a hormone, a growth factor, an enzyme, a clotting factor, an apolipoprotein, a receptor, a drug or an antigen.

15. The vector of claim 5, wherein said 5' flanking region comprises nucleotides 1 to 1540 of Sequence ID No. 1;

said intron and intron/exon boundary comprises nucleotides 1587 to 1679 of Sequence ID No. 1;

said 3' flanking region comprises nucleotides 4384 to 6530 of Sequence ID No. 1; and said linker inserted at the unique Cla I site at nucleotides 2700 to 2705 of Sequence ID No. 2.

16. The vector of claim 5, wherein said 5' flanking region comprises a unique 5' Xho I site up to nucleotide 360 of Sequence ID No. 3;

said intron and intron/exon boundary comprises nucleotides 928 to 1494 of Sequence ID No. 3;

said 3' flanking region comprises from nucleotide 4740 of Sequence ID No. 3 to a unique 3' Xho I site; and said linker inserted between nucleotides 1504 to 1509 of Sequence ID No. 3.

17. The vector of claim 1 or 4, wherein said vector further comprises a vitamin D regulatory element associated with said 3' or 5' flanking regions.

18. The vector of claim 17, wherein said vitamin D regulatory element is from a K1 keratin gene.

19. The vector of claim 1 or 4, wherein said vector further comprises a vitamin A regulatory element associated with said 3' or 5' flanking regions.

20. An isolated or cultured mammalian epidermal cell transformed with a vector for expression of a nucleic acid sequence, wherein said nucleic acid sequence is other than a mammalian loricrin gene or a mammalian K6 keratin gene, said vector comprising, in operable association:

a 5' flanking region from a mammalian gene including necessary sequences for expression of said nucleic acid sequence;

a 3' flanking region from a mammalian loricrin gene or a mammalian K6 keratin gene which regulates expression predominantly in an epidermal cell of said nucleic acid sequence with which it is associated; and a linker connecting said 5' flanking region to said nucleic sequence, said linker having a position for inserting said nucleic acid sequence, wherein said linker lacks the coding sequences of a gene with which it is naturally associated.

21. The mammalian epidermal cell of claim 20, wherein said nucleic acid sequence comprises genetic material coding for a protein or a polypeptide.

22. The mammalian epidermal cell of claim 21, wherein said genetic material codes for a hormone, a growth factor, an enzyme, a clotting factor, an apolipoprotein, a receptor, a drug or an antigen.

23. The mammalian epidermal cell of claim 20, wherein said vector further comprises a vitamin D regulatory element.

24. The mammalian epidermal cell of claim 20, wherein said vector further comprises a vitamin A regulatory element.

* * * * *

SEQUENCE LISTING (1) GENERAL INFORMATION:

(iii) NUMBER OF SEQUENCES:  4

(2) INFORMATION FOR SEQ ID NO: 1:

(i) SEQUENCE CHARACTERISTICS:
      (A) LENGTH:                6530 bases
      (B) TYPE:                  nucleic acid
      (C) STRANDEDNESS:          single
      (D) TOPOLOGY:              linear (ii) MOLECULE TYPE:          DNA (genomic)

(xi) SEQUENCE DESCRIPTION:  SEQ ID NO: 1:

```
GGATCCTGAT ATAGCTGTCT CTTTTGAGAC TATCCCGGGG CCTAGCAAAC ACAGAAGTGG      60

ATGCTCACAG TCAGGGATTG GGTGAATCAC AGGGCCCCCA ATGTTGGAGC TAGAGAAAGA     120

ACCCAGGGAG CTGGGGGGAT CACCTGAGTT CATACTGTCC AAACTGAAAC AAGTGGCACA     180

AGTTTCTGAG AGCCAAAGTC TAATCAGGAT CGTTTAGATC ATTAATGCTC CCCCATAATT     240

AAGACAATTT CTGATTAGAA TTATTCTTTC AACACAGCTG GGTGGAACAA GGTTCAACAG     300

TGGTATCTTA ATAGCAACTG AGTTCCAATG ATGAAAGAAA GGAAAAACAC TATGTTCTTC     360

ATACACAGAG GGGGGCTGCT CTTGGCCCTA GGGTCATCAG AGAACTGAGT AAATCTTATA     420

GGAAAATAGT TAAGATGTCT TCACACACCT CCTTTCCAAT AGGGTTCAAG GGCAGGCATG     480

ATTGGAAGGA AAAGTGTTCT GTCATGTGAG AAAAGAGCAA AAGTATTAAT ATCACATACT     540

ATGTAGTACA TTCATATTTC ATAACTTCCA TTTTCATGTT TCTGTGAAAT AAATTATAGG     600

ATTCCTGCTT GGTAGACCAA ATGGGGATCA GACAGCTCAA CAATGAACAA GTACTCAGTA     660
```

| | |
|---|---|
| ACTGCCCTGT TGGTGGCATT GCATGAACTA CTGTGCTTTG CCCATGGTGA CATAGCTTGA | 720 |
| AATAGTAATG GAAGACCTGA ACCCAACTGA GATCTCTAAG TACATTCCAC TCTATGGTGG | 780 |
| CATCTCAGAG GTCAGAGTCA CTGTGCAGCG CCATAGGACA TCAGAATCAA AGGGTCATGG | 840 |
| TGAAAAGGCT GCCAGGGTCT GTCTTGTTAG TTCTCACCTT TGTAAGTAAA GTCAGTAGTC | 900 |
| AGTAACAAAG ATCAAAACAC CTGCTCTCAC AAGGAATAAC TTAAAGTAGA CTAAAGTCAT | 960 |
| GCTAGTTACA GTGCTGTCTT TTCCGTGGTA CCATCCCAAA CTGGGAGCTG GGACTCACG | 1020 |
| AACTCTCACA ACCAATAAAG TAAGCAGAAC AGAAGCAACC CAATGAAGTG TTCATGAAAC | 1080 |
| TGGAATGGAG AAATTGTGGC ATAAGAGATG GATTCTAAAA TTTTGAGAAT TTCCAAGATA | 1140 |
| ATGAAATTAA AACCAAACAT CAAAATTGGA AAGATACAAC TGAACTAGCT TCTATGTCTT | 1200 |
| AGACAATGTC TTAGATCTCT AGATTCCGTA AGGCTGCTTC ACAAGTCTGC AACCTAGTCC | 1260 |
| TCTAGAATAG CCCTCTGGTT ATGGCACGCA ACCTATACAG AAGTTTTGAA AACAATTTCT | 1320 |
| GCCATCCACA CTGCTGGCCA TCTCTAATGA CCAACCTGCT CACTGTTACA TCAGAGAAGT | 1380 |
| GGCCAGTCAT ACACCAAACT GCCTATCCCT ATCCCAAGAA TTTGAAATCT TCATGAATGG | 1440 |
| GTCAATCCTT CCCCTGCAAT CACAGGGAGG AGGTGCCTGA TCAATAGATG AGTCAGAGCA | 1500 |
| GGACAAGAGT ATAAAACACA GGAGCACCAG TGTCCCTCAC ATCAGCATCA CCTCCTTCCC | 1560 |
| TCACTCATCT TCCCTGGTGC TTCAGGTAAG GTGTGGGCTCT CCTGGCTGTC TGGTCTCTCC | 1620 |
| AGTTGGCCTT GCTCAGCTTG CAGAGAGGTT AAGGAACAGA GCCTTTCTCC CCTTTGGAAG | 1680 |
| GTACTCTGTT CAAATTGAGA AGGGCTTTAG GAAAGCACTG GGAGAGTGGT AAGCTGGTGC | 1740 |
| TGGGCAGATG ATGTGTCTGG TCTTCTGGGC AGAATGTTAA AACTTCACAA AGATATGACT | 1800 |
| ATCTCCTACT TCTCTGGCAC CCTGGGAGCT GAGGGTTAGA ATACTGGATG ACTGCAGTGG | 1860 |
| CAGGCCTCCA TGGGCTGGAT GAACCTTTTG AACCTGCCAG AAGTGGCTGA ATACACTATC | 1920 |
| AGGAAGGGAG AGGGACGATA AGTCATAGAA TGGTGCTGAT GGGAGATTTG AGAAGCCACA | 1980 |
| AAAACCCAAG CTCTGCTTTA TGAGGGCAGA TGTTCTGACA GATAAATGAC TTGTGAGGTG | 2040 |
| CTGAACTACA CAGCTTCCTA TTAGCTACAG CTAATTGGAG TCTACCAAAT TTAGACTCCT | 2100 |
| GCATATCTCA AAAAGATGTC TACTTTCTTC TGGTTAGATG TACTGGTCCA AAAGGTTCAG | 2160 |
| AGTTCTTCCA TTTGTTTGCA GACAGGACCA CAGTAGAGCT GTCTTGTCTA ATAATTGGCC | 2220 |
| CTTGGAGGAT ATCTCACTCA ATAGGACAGA TCAAGAGTTT AAACTAAGGA CTTTATACAG | 2280 |
| GAAATGCTAA TGTCCAAACA AATCTTTTCT TATTGTGCTG GGAGTGGATA AAATCCACGT | 2340 |
| GGAATTTTTG CAACTTTCTA CTGAATTTAA AGAATCAGCA CTGGGACTTG GGAGCACCCT | 2400 |
| TAGACATGGA GTGTTTATTA ATGTAAGATC AAAAGCAGGT GGGAATGTGG GGGTTCTGCT | 2460 |
| TCCCAAATCA CATAGTAGAA GAAAGGCAGA GTTGAGGGAA AAGGGGGTCA CTATTAACGG | 2520 |
| GACTTTTGAA GAGCTAACCA GTCCAGGAAT GGAGTCCAGA CACCTAGTCT GCATAAAGCT | 2580 |
| AGGAGTCAGA AGTATGTTGG CATGGATGCA TCTGCCACCT TCACAGCGTC CTCTTGCTGC | 2640 |
| TGTTGGTCTA ATGTTGCTCT TCTGCTCTTC TTCCAGGGTT CCCCTTCTCC TTAAACAAGA | 2700 |
| TGTCTCACCA GAAAAAGCAG CCCACTCCCT GCCCTCCTGT GGGTTGTGGA AAGACCTCTG | 2760 |
| GTGGAGGAGG AGGCGGCGGC GGCTATTATA GCGGTGGCGG CTCTGGCTGC GGAGGCGGCT | 2820 |
| CATCTGGAGG AGGCTCTAGC TGTGGAGGCG GAGGCGGTGG TTCCTATGGA GGTGGTTCCA | 2880 |
| GCTGCGGCGG TGGAGGCGGC TCCGGTGGGG GCGTCAAGTA CTCCGGAGGC GGCGGTGGCT | 2940 |
| CTAGCTGCGG CGGCGGCTAC TCCGGAGGCG GTGGTGGCTC TAGCTGCGGC GGTGGCTACT | 3000 |
| CTGGGGGCGG CGGCGGCTCC AGCTGCGGAG GTGGCTACTC CGGAGGCGGC GGCGGCTCCA | 3060 |

```
GCTGCGGCGG CGGCAGCTAC TCCGGGGTG  GCTCCAGCTG TGGAGGCGGT GGCGGCTCTG    3120

GTGGGGCGT  CAAGTACTCC GGAGGTGGTG GCGGCGGCGG CTCTAGCTGC GGCGGCGGCT    3180

CCTCCGGGG  CGGCGGCGGC GGCTCCAGCT GCGGAGGCGG ATCAGGAGGC GGCGGCTCCT    3240

ACTGCGGAGG CTCCTCTGGA GGCGGCAGCT CCGGTGGCTG CGGCGGCGGT TCCGGAGGCG    3300

GCAAGTACTC TGGTGGCGGC GGTGGCTCCA GCTGCGGAGG CGGCTATTCC GGCGGCGGTG    3360

GAAGCAGCGG CGGCTCTAGC TGTGGCGGCG GCTACTCAGG TGGCGGTGGA TCCAGCTGCG    3420

GCGGCGGCGG CGGCTATTCC GGTGGCGGCG GCACGAGCTG CGGAGGTGGT TCCTCCGGTG    3480

GCGGCGGCGG CGGATCGTCC CAACAGTATC AGTGCCAGAG CTACGGAGGC GGTTCTAGCG    3540

GTGGCTCCAG CTGCGGCGGC GGCTACTCCG GGGGCGGAGG CTCCAGCTGC GGTGGCGGCT    3600

ACTCCGGGGG CGGAGGCTCT AGCTGCGGAG GCGGCTCCTC TGGTGGTGGC TCCAGTTGCG    3660

GCGGCAGCGG CGGCGGCGGC TATTCCGGTG GTGGCGGTGG CAGCTGCGGC GGCGGCTCCT    3720

CTGGCGGCGG AGGGGGCTAT TACTCCTCTC AGCAGACCAG TCAGACCTCC TGCGCCCCCC    3780

AGCAGAGCTA CGGAGGGGGC TCTTCCGGAG GAGGTGGTAG CTGTGGAGGT GGCTCCTCTG    3840

GCGGCGGTGG CGGCGGTGGC TGCTACTCCA GCGGTGGTGG CGGCAGCAGC GGTGGCTGCG    3900

GTGGAGGCTA CTCCGGAGGC GGCGGTGGCT GTGGCGGCGG CTCTTCCGGG GGCAGCGGCG    3960

GTGGCTGCGG AGGTGGCTCT TCCGGAGGCA GCGGCGGTGG CTGCGGAGGA GGCTACTCCG    4020

GAGGCGGAGG CGGTGGCTCC AGCTGCGGAG GCGGCTCCTC TGGTGGCGGC TCTGGAGGTG    4080

GCAAGGGTGT GCCAGTCTGC CACCAGACCC AGCAGAAGCA GGCGCCTACC TGGCCGTGCA    4140

AGTAAGGTCA CCGGGTTGCA ACGGAGACAA CAGAGCTGGA AGAGTTCTCC GTGGGCGCCG    4200

ATGGGCTTAA CTTTCTCATG AATTTGCCTG AGGTTTCCAA ACCCTTCACA TTTTAAGCGC    4260

CCCTTCCCCC AGAAGAAGCC ATTGAGTCGC TCAAGGTGTA TCCTGTTCTG CAGATTTTTC    4320

ATCTTGGTTT CTGAATGACT ACCTCCCAAT TCTAGTGTCT CCTCAGTCAA TAAATTTGCT    4380

ATTCATGAGA ATCTCTGAGT TTGCTGTAGT CTTTGTAGCT TGCAAATTTA CTCAGTTCAT    4440

TCTGTGTTTG CTTTTTCCAT TCATTAGTTC ACATTTAAAT TCACTGAACA AGTGTTCTAT    4500

CCCAAGGTGG GGGAGTAGAT AGATGGAATG GGCAAAGGA  TGACCAAGGT TGTGAACAGT    4560

CTGGGGTGTG GCTTAAAAAT CATGAGATGG TCCTCAAACA CCAAGAAAAG TCTTCACTGG    4620

ACATCCTACA CATCACTGAA ATTGGGCCTG CGCAGGCAAT TTCTAGCAGT GCAGAGTTCA    4680

CTCTCCAAGT TCTGGAAGCA GGATGGCTCT CAGATTAGGT TAGCTACCAG AGGTCCAAGT    4740

CCACTGACAT GTTCTGACCT AAGAAGAAGG ACATTCACCC CTGAACAAAA GACCCCTGCC    4800

CATGCGATCT TCCGGAACAC TATAACTACT TTCCTTACTC ATGACCCATG ATAGAGCTTT    4860

GAGGCAAAGA TACAAACCCT CTATGTCTTC TCAAGATTGC CAGTTCTTCA TTAAGCCTGA    4920

TACCTTCTTA CCAGCGCACG TCTCCTGAAT ACTGATAAAG TCTGGTTTTG TTAGTCTGTT    4980

AGAAAAATAT TATATCAGAT AATCAAGATC CTCTACAGTG TGTGAGACAG TTTACTGAGC    5040

ATCTATAGAG ATAGAAGGCA GCCCTCTTGA AGGATTGAAC GCGTACGTTT CGTCCAATTT    5100

GAGAAGGTAC ATCGTAAGTA TTTAAGATGC TTAACATCAG TATCACAGAG GTCACTGGAA    5160

ACATTAGGGG CCTCCTGATT AGCAAGCATA AAGCTAGAGT TGCTCAAAGG CATGTGTAAC    5220

AACCATCCCC TGGCCAGATC CTGTTTTACA GTCAGATTTT ATCAGCTTTA GGTAAATGCT    5280

AACTTACTGA CTTACTCAAG TTAATTTTGC TATACTAAAA AGCCAATGTG CCTTCCTACA    5340

TTTAGCTAAT GATAGAAATA AAAAGATTTC ATCTCACTCT TCCATTTGGA GTCATCACTA    5400

CCTTCATCAT TTGCATCAGA GATAGAGCAT GCCAAGTAGC AACCTCAGTG ACACAGTAGT    5460
```

-continued

```
CTTACCACCA CATTTTTATG GATTAAATGT ATTTTTTTTA GCATGGTTAT ATGTGCATAT      5520

AATACACTCT GATTACTCAC TTCCCTATCC TTTCTTACTC CTCCCCATCC CAACCTGTAT      5580

CAATCCTTAC CTTCCCTACA ATTCCCTTTA CCATGTTTTT GTTAGTTTTG TTGGTTTGTT      5640

TTGTGACCCA CTGAGCTAAC CAGGGCCATC TGTATGACCA TGGGTTTGGA TTCTGATGGA      5700

ATCCCACTGG GTACACAACT GAAACTAGTG ACTCCCCTTC ACAGAATCTA TCAGTAGACA      5760

ATAATTCAAC AGGGAATGGT GGGGCTCTCT CCATCCTTGG CTAACTGTTG ACAGGACAGT      5820

CTTGTGCAGG CCTAGTGCAG ACAACCATAG TTGCTGTGAG CTCATGTTTG CAATGGCTGT      5880

GTTATACATA GGAGATAGTA TTTTGGAGCC ATTATCCATG TCTGGCTCTT ATATTCCACC      5940

TTCTCTTTTA GGATGTTCCT TGAGTCTTTG AGGAATGTTT TGGTTAGAAC CGAGTGCTCA      6000

GTTGTCATTT ATTTTCAGAA TCTTGAGCAT CAAAGGATAC ATAAGATATT ATATTATAGG      6060

ATACTAAATT TTTGTACAGA TTTTTCATAT ACCCTTCATA TTGGTTAACC ATAATCCCCA      6120

ATTTTTCTCT CCTCTAACAC TCCACTGCTC CCATACCAGA TGAAACCTTT CAACTCCATG      6180

TATTTTCCCT CTTTGCTTTC ATTTTATCTA TATTGTATGA TCTCAACTCC CTTAATCTAT      6240

CTCACTACCA ATAACCCTTT TCTAAACTGG TAGCCTACAA CTTTAGTTCC AGTACTTGAT      6300

GCAGAAGTAG ATGGAGCAAT GTGAACTCAT GCTCAGCCTG GTCTATGGAA TGGGTTACAA      6360

GCCAGCCCGG ACTATGTAAT AGGACCCTGT CTCAAAAACA ACTAAACCAA ACAAACAAAC      6420

AAACAAAGAA CAAACAAACA AACAAACCAA AAATCTCAAC CATTTCTAGT TTTTCTAGTT      6480

TTTACTTGAA CATCAAGTTA AGCATAACTA AAGTTTCAAA AATAGGATCC                 6530
```

(2) INFORMATION FOR SEQ ID NO: 2:

(i) SEQUENCE CHARACTERISTICS:
        (A) LENGTH:         5092 bases
        (B) TYPE:           nucleic acid
        (C) STRANDEDNESS:   single
        (D) TOPOLOGY:      linear (ii) MOLECULE TYPE:       DNA (genomic)

(xi) SEQUENCE DESCRIPTION: SEQ ID NO: 2:

```
GGATCCTGAT ATAGCTGTCT CTTTTGAGAC TATCCCGGGG CCTAGCAAAC ACAGAAGTGG       60

ATGCTCACAG TCAGGGATTG GGTGAATCAC AGGGCCCCCA ATGTTGGAGC TAGAGAAAGA      120

ACCCAGGGAG CTGGGGGGAT CACCTGAGTT CATACTGTCC AAACTGAAAC AAGTGGCACA      180

AGTTTCTGAG AGCCAAAGTC TAATCAGGAT CGTTTAGATC ATTAATGCTC CCCCATAATT      240

AAGACAATTT CTGATTAGAA TTATTCTTTC AACACAGCTG GGTGGAACAA GGTTCAACAG      300

TGGTATCTTA ATAGCAACTG AGTTCCAATG ATGAAAGAAA GGAAAAACAC TATGTTCTTC      360

ATACACAGAG GGGGGCTGCT CTTGGCCCTA GGGTCATCAG AGAACTGAGT AAATCTTATA      420

GGAAAATAGT TAAGATGTCT TCACACACCT CCTTTCCAAT AGGGTTCAAG GGCAGGCATG      480

ATTGGAAGGA AAAGTGTTCT GTCATGTGAG AAAAGAGCAA AGTATTAAT ATCACATACT       540

ATGTAGTACA TTCATATTTC ATAACTTCCA TTTTCATGTT TCTGTGAAAT AAATTATAGG      600

ATTCCTGCTT GGTAGACCAA ATGGGGATCA GACAGCTCAA CAATGAACAA GTACTCAGTA      660

ACTGCCCTGT TGGTGGCATT GCATGAACTA CTGTGCTTTG CCCATGGTGA CATAGCTTGA      720

AATAGTAATG GAAGACCTGA ACCCAACTGA GATCTCTAAG TACATTCCAC TCTATGGTGG      780

CATCTCAGAG GTCAGAGTCA CTGTGCAGCG CCATAGGACA TCAGAATCAA AGGGTCATGG      840

TGAAAAGGCT GCCAGGGTCT GTCTTGTTAG TTCTCACCTT TGTAAGTAAA GTCAGTAGTC      900

AGTAACAAAG ATCAAAACAC CTGCTCTCAC AAGGAATAAC TTAAAGTAGA CTAAAGTCAT      960
```

```
GCTAGTTACA GTGCTGTCTT TTCCGTGGTA CCATCCCAAA CTGGGAGCTG GGACTCACG    1020

AACTCTCACA ACCAATAAAG TAAGCAGAAC AGAAGCAACC CAATGAAGTG TTCATGAAAC   1080

TGGAATGGAG AAATTGTGGC ATAAGAGATG GATTCTAAAA TTTTGAGAAT TTCCAAGATA   1140

ATGAAATTAA AACCAAACAT CAAAATTGGA AGATACAAC TGAACTAGCT TCTATGTCTT    1200

AGACAATGTC TTAGATCTCT AGATTCCGTA AGGCTGCTTC ACAAGTCTGC AACCTAGTCC   1260

TCTAGAATAG CCCTCTGGTT ATGGCACGCA ACCTATACAG AAGTTTTGAA ACAATTTCT    1320

GCCATCCACA CTGCTGGCCA TCTCTAATGA CCAACCTGCT CACTGTTACA TCAGAGAAGT   1380

GGCCAGTCAT ACACCAAACT GCCTATCCCT ATCCCAAGAA TTTGAAATCT TCATGAATGG   1440

GTCAATCCTT CCCCTGCAAT CACAGGGAGG AGGTGCCTGA TCAATAGATG AGTCAGAGCA   1500

GGACAAGAGT ATAAAACACA GGAGCACCAG TGTCCCTCAC ATCAGCATCA CCTCCTTCCC   1560

TCACTCATCT TCCCTGGTGC TTCAGGTAAG TGTGGGCTCT CCTGGCTGTC TGGTCTCTCC   1620

AGTTGGCCTT GCTCAGCTTG CAGAGAGGTT AAGGAACAGA GCCTTTCTCC CCTTTGGAAG   1680

GTACTCTGTT CAAATTGAGA AGGGCTTTAG GAAAGCACTG GGAGAGTGGT AAGCTGGTGC   1740

TGGGCAGATG ATGTGTCTGG TCTTCTGGGC AGAATGTTAA AACTTCACAA AGATATGACT   1800

ATCTCCTACT TCTCTGGCAC CCTGGGAGCT GAGGGTTAGA ATACTGGATG ACTGCAGTGG   1860

CAGGCCTCCA TGGGCTGGAT GAACCTTTTG AACCTGCCAG AAGTGGCTGA ATACACTATC   1920

AGGAAGGGAG AGGGACGATA AGTCATAGAA TGGTGCTGAT GGGAGATTTG AGAAGCCACA   1980

AAAACCCAAG CTCTGCTTTA TGAGGGCAGA TGTTCTGACA GATAAATGAC TTGTGAGGTG   2040

CTGAACTACA CAGCTTCCTA TTAGCTACAG CTAATTGGAG TCTACCAAAT TTAGACTCCT   2100

GCATATCTCA AAAAGATGTC TACTTTCTTC TGGTTAGATG TACTGGTCCA AAAGGTTCAG   2160

AGTTCTTCCA TTTGTTTGCA GACAGGACCA CAGTAGAGCT GTCTTGTCTA ATAATTGGCC   2220

CTTGGAGGAT ATCTCACTCA ATAGGACAGA TCAAGAGTTT AAACTAAGGA CTTTATACAG   2280

GAAATGCTAA TGTCCAAACA AATCTTTTCT TATTGTGCTG GGAGTGGATA AAATCCACGT   2340

GGAATTTTTG CAACTTTCTA CTGAATTTAA AGAATCAGCA CTGGGACTTG GGAGCACCCT   2400

TAGACATGGA GTGTTTATTA ATGTAAGATC AAAAGCAGGT GGGAATGTGG GGGTTCTGCT   2460

TCCCAAATCA CATAGTAGAA GAAAGGCAGA GTTGAGGGAA AAGGGGGTCA CTATTAACGG   2520

GACTTTTGAA GAGCTAACCA GTCCAGGAAT GGAGTCCAGA CACCTAGTCT GCATAAAGCT   2580

AGGAGTCAGA AGTATGTTGG CATGGATGCA TCTGCCACCT TCACAGCGTC CTCTTGCTGC   2640

TGTTGGTCTA ATGTTGCTCT TCTGCTCTTC TTCCAGGGTT CCCCTTCTCC TTAAACAACA   2700

TCGATAAGGT CACCGGGTTG CAACGGAGAC AACAGAGCTG GAAGAGTTCT CCGTGGGCGC   2760

CGATGGGCTT AACTTTCTCA TGAATTTGCC TGAGGTTTCC AAACCCTTCA CATTTTAAGC   2820

GCCCCTTCCC CCAGAAGAAG CCATTGAGTC GCTCAAGGTG TATCCTGTTC TGCAGATTTT   2880

TCATCTTGGT TTCTGAATGA CTACCTCCCA ATTCTAGTGT CTCCTCAGTC AATAAATTTG   2940

CTATTCATGA GAATCTCTGA GTTTGCTGTA GTCTTTGTAG CTTGCAAATT TACTCAGTTC   3000

ATTCTGTGTT TGCTTTTTCC ATTCATTAGT TCACATTTAA ATTCACTGAA CAAGTGTTCT   3060

ATCCCAAGGT GGGGGAGTAG ATAGATGAA TGGGCAAAG GATGACCAAG GTTGTGAACA    3120

GTCTGGGGTG TGGCTTAAAA ATCATGAGAT GGTCCTCAAA CACCAAGAAA AGTCTTCACT   3180

GGACATCCTA CACATCACTG AAATTGGGCC TGCGCAGGCA ATTTCTAGCA GTGCAGAGTT   3240

CACTCTCCAA GTTCTGGAAG CAGGATGGCT CTCAGATTAG GTTAGCTACC AGAGGTCCAA   3300

GTCCACTGAC ATGTTCTGAC CTAAGAAGAA GGACATTCAC CCCTGAACAA AAGACCCCTG   3360
```

```
CCCATGCGAT CTTCCGGAAC ACTATAACTA CTTTCCTTAC TCATGACCCA TGATAGAGCT    3420

TTGAGGCAAA GATACAAACC CTCTATGTCT TCTCAAGATT GCCAGTTCTT CATTAAGCCT    3480

GATACCTTCT TACCAGCGCA CGTCTCCTGA ATACTGATAA AGTCTGGTTT TGTTAGTCTG    3540

TTAGAAAAAT ATTATATCAG ATAATCAAGA TCCTCTACAG TGTGTGAGAC AGTTTACTGA    3600

GCATCTATAG AGATAGAAGG CAGCCCTCTT GAAGGATTGA ACGCGTACGT TTCGTCCAAT    3660

TTGAGAAGGT ACATCGTAAG TATTTAAGAT GCTTAACATC AGTATCACAG AGGTCACTGG    3720

AAACATTAGG GGCCTCCTGA TTAGCAAGCA TAAAGCTAGA GTTGCTCAAA GGCATGTGTA    3780

ACAACCATCC CCTGGCCAGA TCCTGTTTTA CAGTCAGATT TTATCAGCTT TAGGTAAATG    3840

CTAACTTACT GACTTACTCA AGTTAATTTT GCTATACTAA AAAGCCAATG TGCCTTCCTA    3900

CATTTAGCTA ATGATAGAAA TAAAAAGATT TCATCTCACT CTTCCATTTG GAGTCATCAC    3960

TACCTTCATC ATTTGCATCA GAGATAGAGC ATGCCAAGTA GCAACCTCAG TGACACAGTA    4020

GTCTTACCAC CACATTTTTA TGGATTAAAT GTATTTTTTT TAGCATGGTT ATATGTGCAT    4080

ATAATACACT CTGATTACTC ACTTCCCTAT CCTTTCTTAC TCCTCCCCAT CCCAACCTGT    4140

ATCAATCCTT ACCTTCCCTA CAATTCCCTT TACCATGTTT TTGTTAGTTT TGTTGGTTTG    4200

TTTTGTGACC CACTGAGCTA ACCAGGGCCA TCTGTATGAC CATGGGTTTG GATTCTGATG    4260

GAATCCCACT GGGTACACAA CTGAAACTAG TGACTCCCCT TCACAGAATC TATCAGTAGA    4320

CAATAATTCA ACAGGGAATG GTGGGGCTCT CTCCATCCTT GGCTAACTGT TGACAGGACA    4380

GTCTTGTGCA GGCCTAGTGC AGACAACCAT AGTTGCTGTG AGCTCATGTT TGCAATGGCT    4440

GTGTTATACA TAGGAGATAG TATTTTGGAG CCATTATCCA TGTCTGGCTC TTATATTCCA    4500

CCTTCTCTTT TAGGATGTTC CTTGAGTCTT TGAGGAATGT TTTGGTTAGA ACCGAGTGCT    4560

CAGTTGTCAT TTATTTTCAG AATCTTGAGC ATCAAAGGAT ACATAAGATA TTATATTATA    4620

GGATACTAAA TTTTTGTACA GATTTTTCAT ATACCCTTCA TATTGGTTAA CCATAATCCC    4680

CAATTTTTCT CTCCTCTAAC ACTCCACTGC TCCCATACCA GATGAAACCT TTCAACTCCA    4740

TGTATTTTCC CTCTTTGCTT TCATTTTATC TATATTGTAT GATCTCAACT CCCTTAATCT    4800

ATCTCACTAC CAATAACCCT TTTCTAAACT GGTAGCCTAC AACTTTAGTT CCAGTACTTG    4860

ATGCAGAAGT AGATGGAGCA ATGTGAACTC ATGCTCAGCC TGGTCTATGG AATGGGTTAC    4920

AAGCCAGCCC GGACTATGTA ATAGGACCCT GTCTCAAAAA CAACTAAACC AAACAAACAA    4980

ACAAACAAAG AACAAACAAA CAAACAAACC AAAAATCTCA ACCATTTCTA GTTTTTCTAG    5040

TTTTTACTTG AACATCAAGT TAAGCATAAC TAAAGTTTCA AAAATAGGAT CC            5092

(2) INFORMATION FOR SEQ ID NO: 3:

(i) SEQUENCE CHARACTERISTICS:
        (A) LENGTH:          5159 bases
        (B) TYPE:            nucleic acid
        (C) STRANDEDNESS:    single
        (D) TOPOLOGY:        linear (ii) MOLECULE TYPE:      DNA (genomic)

(xi) SEQUENCE DESCRIPTION: SEQ ID NO: 3:

GGGAAAACCT GTGTGGTGAG GGGGCACACA GGGAGTGTCT ACATGGGGCA AGAAGGAAAG       60

GGACAATTAT CACAGATCAG CTCCTTGTCT CTTTTGTTTG AGAAGATGAC TAACTCATGA      120

CTTAAGAGAA TTTACGTCCT GGCTCATTGT GTTCAGATCA AGTCAAGGCT GGAAGGCAGG      180

AGAATTTGCT CCGTGACTAA AGGAATCCAA AAGCAATCTT CATGTATCAT ACCTTTCTAG      240
```

| | |
|---|---|
| AACTTGGGGG TGATCTCATT ATTTGTAAAG CCCTGCCCTA CCCACTCTGC AAGCTCACCA | 300 |
| TCAGGACCCA ACCCAGCCCA TCTGTACCAT ATATAAGCGG CTGCCCAGAG CTCAACACAC | 360 |
| TCATCTCTTC AGCTCTGCCC TGCCGTTTCT CTACTTCCCA GCCTTCTCAT CTCCAGGAAC | 420 |
| CATGTCTACC AAAACCACCA TCAAAAGTCA AACCAGCCAC CGTGGCTACA GTGCCAGCTC | 480 |
| AGCCAGAGTG CCTGGGCTCA ACCGCTCTGG CTTCAGCAGT GTGTCCGTGT GCCGCTCCCG | 540 |
| GGGCAGCGGT GGCTCCAGTG CAATGTGTGG AGGAGCTGGC TTTGGCAGCA GGAGCCTCTA | 600 |
| TGGTGTGGGG AGCTCCAAGA GGATCTCCAT CGGAGGGGGC AGCTGTGGCA TTGGAGGAGG | 660 |
| CTATGGCAGC CGATTTGGAG GAAGCTTCGG CATTGGAGGT GGAGCTGGTA GTGGCTTTGG | 720 |
| CTTCGGTGGT GGAGCTGGCT TTGGTGGTGG CTATGGGGGA GCTGGCTTCC CGGTGTGCCC | 780 |
| ACCTGGAGGC ATCCAAGAGG TCACCATCAA CCAGAGCCTC CTCACACCCC TGAACCTGCA | 840 |
| AATTGACCCC ACCATCCAGC GGGTCAGGAC TGAGGAGAGG GAGCAGATCA AGACCCTCAA | 900 |
| TAACAAGTTT GCCTCCTTCA TCGACAAGGT GAGACATGGT CCTCCCTAGA GCACCCTGTG | 960 |
| TGTCTACAGG GAATGCTGAA CAGAGGTGTA GGGAAGAGGC TTCAGTCTCA GCTCTGATAC | 1020 |
| TGCCTGTGTT GCTAGTTGAT GCTCTGTCCT GGTTTGTGTT CCTCTTCAGT TAGACTGGCA | 1080 |
| TCTGGAAATC AGGGTCAGCG TTCCTCTCCT CCAGAGGTTG CCCTATAAGG GTGTCTGGTC | 1140 |
| CCAGTGGACT GAGATGACTT AAAGACTCAC AAAACAGGCT TGTAGGGAAA TGGAAGATTA | 1200 |
| TAACTATGTA TAGTGCAGTT GGGAGGCATG CCAGCCTCAC TAAGCTGCAG CACACTTCAT | 1260 |
| CAAGCCATGG CTAACCTGCC AGTGCCCTAC ATGAGTTCTC TGCCCTCCTT AGAGAGGTGG | 1320 |
| CATTGGGTGC TTCAGTCTGG ACTGTTTCCC TCAGACCCAG GGTCAGGGTC TAACTACACT | 1380 |
| GAATGAGTTT AGTCAGACAG CCTGAGAGGG TACACACACT AGTGAAGTGT TCATAGAAGG | 1440 |
| ATGAAACCCA AACTTCTCCC CCTCATACTT GCCCCCCCGC CCCCACCAGG TGCGGTTCCT | 1500 |
| GGAGCAGCAG AACAAGGTCC TGGACACCAA GTGGGCCCTG CTGCAAGAGC AGGGCACCAA | 1560 |
| GACCGTGAGG CAGAACCTGG AGCCTATGTT TGAGCAGTAC ATCAGCAACC TCCGCAGACA | 1620 |
| GCTGGACAGC ATCATTGGAG AGAGGGGTCG CCTGGACTCA GAGCTGAGGA ACATGCAGGA | 1680 |
| CACAGTGGAG GACTACAAGA GCAAGTGAGT TACAAAGAAG GGAGAATCCA GTCTCCGGAC | 1740 |
| TTTATAAAAA TGGAAGCCCA AATCTAAACA AGGGCTCCAT GATGTAAGAA AGCTTGGTCA | 1800 |
| CATCTGGGAC AGAGGCTGCC ATTGATACCA TCCACCCCGT GGCTCCAATA TAGTGCACCT | 1860 |
| TTCCTCTTGT AGATATGAAG ATGAAATCAA CAAGCGCACA GCAGCAGAGA ATGAATTCGT | 1920 |
| GACCCTGAAG AAGGTGAGTT GACTAACCAC AAGGATGGGT TTCTCTGCGG AATGACATAA | 1980 |
| AAGGCCTTGT ATATCTGCGT CATTCCAGAG AAATGGTGG TACAGGGAAA GAAGTGAACG | 2040 |
| GTCTGGGGAA GAGAGGTAAC CTGATTCCAT GTTCTTGATG GTTTTCTCAG GATGTAGATG | 2100 |
| CTGCCTACAT GAACAAAGTT GAACTGCAAG CCAAGGCAGA CAGTCAACA GATGATATCA | 2160 |
| ACTTCTTGAG AGCTCTCTAT GAAGCAGTAA GCCCCCCTTG TCTTCTCTTC TCCTTTCCAT | 2220 |
| TCACCACTCC CTTTATTTTT TTCCCCCTGG GCAAAGTGTT TGACCTCTGC AGTTCTCAAA | 2280 |
| GACAAAGATG ACTATGGCTC TTTCTGTCCT GCAGGAACTG TCTCAGATGC AAACTCACAT | 2340 |
| CTCAGACACA TCTGTGGTCC TCTCCATGGA CAACAACCGT AGCCTGGACC TGGACAGCAT | 2400 |
| CATCGCTGAG GTCAAGGCCC AGTATGAGGA CATTGCTCAG AGAAGTCGGG CTGAAGCTGA | 2460 |
| GTCCTGGTAC CAGACTAAAG TGAGTATTGG GGTGGAGGCT GATGGGGATG CCTGGGGTCC | 2520 |
| ACCCTGAACT CCATGAGTCT CTGAGTTCAG TATTGGAGGC CCACTAAAAG AAATAGGGAT | 2580 |
| GTTGTCCCAG AAAATGCACT GTGCACATGT ACCATAGAAT AATGTTTTAC TCGAAGAGTA | 2640 |

```
AAAGAACACA GAGGTAGATG CAAAGTTGCC ATAAATGGGG TCCATGCTCT TTGCTTGAGC   2700

TGTACTCTGA ACAATGATCC TCTTGAGAAA CTAGAGAACA TTTTCACTTC CTGAGGGAAC   2760

TATGGAGTCT GTGGTCTCCT AAAGCTTCTC TTGAGGAAAA GCCAGCACAT CCATGGAAGT   2820

GTGTGCCACT CAGAGGTGGG TTTCGTTCCG CATGTAACAA CTCACATAGA TGTCCTCTCT   2880

TTGATTGGCC TTCAGTATGA GGAGCTGCAG GTCACAGCTG GCAGACATGG GGACGACCTG   2940

CGCAACACCA AGCAGGAGAT TGCTGAGATC AACCGCATGA TCCAGAGGCT GAGATCTGAG   3000

ATCGACCACG TTAAGAAGCA GGTGGGGTAG ACAGAGAAAT GCATGGGTTG CGGGTTGTGT   3060

TTCCTGTCCT CTAACTCTTG CTCACCAGAA ACCATGGTCT GGGGCTCAGC CTCTGCAGAG   3120

ATGTACACTC CACGATTATT TTTGTTGCTC TCTCTGCCCA GTGTGCCAAC CTGCAAGCTG   3180

CTATTGCTGA TGCTGAGCAA CGTGGGGAGA TGGCCCTGAA GGATGCCAGG GGCAAGCTGG   3240

AAGGGCTGGA GGATGCCCTG CAGAAGGCCA ACAGGACAT GGCCAGGCTG CTGAAGGAGT   3300

ACCAGGAACT CATGAATGTC AAGCTGGCCC TGGATGTGGA AATTGCCACC TACAGGAAGC   3360

TGCTGGAAGG AGAGGAGTGC AGGTGGGTAA CTATATCCTC CAACCCCTGA GGACAGCTCC   3420

TTGGTGCAAG CACTGAGCAC AAGAAGGGAG CACTGACTAT GCCCACAATA GTCCCTTTAA   3480

GAAACTCCTT GCTGTGCTGG AGAGATGGCT CATTGTTTAA GAGCACTAAC TCCTCTTCCA   3540

GAGTTACTGA GTTTAATTCC CAGCAACCAC CTGGTGATTC ACAATCATCT CTATTGAGAT   3600

CCAGTGCCCC CTTCTGGTGT GTTTGAAAAC AGCTACAGTG AACTAAAATA CATATACTAA   3660

ATAAAGAATA TTTTTAAACA AACAAACAAA ACAAAACAAA CAAACAAACA ATCAACCCAA   3720

AACAAAACTC TAGTGGATTC TCTCTGAGCC TTCACTAGAT TGAGGCTTCC CATTCAGGCT   3780

GAAGTGATGG CTGCCTAGTT CTCACCTGTT GCTTTCCTCT TGTAGGTTGA ATGGTGAAGG   3840

TGTTGGACCA GTCAACATCT GTAAGTACTC TGCTTGTCCG AATCCCCTTC TCCTTACTTT   3900

GTGGCTTAAT TATCTGGTCA CAGTGGGCTG ACCATGTCTG TGGTGTCCTT TTCCTCCTTC   3960

ACAGCTGTGG TGCAGTCCAC CGTGTCCAGC GGCTATGGCA GTGCCGGGGG TGCCAGCAGC   4020

AGCTTAGGCC TGGGTGGAGG CAGCAGCTAC TCCTATAGCA GCAGCATGG CCTTGGAGGT   4080

GGCTTCAGTG CTGGCAGTGG CAGAGCCATC GGAGGTGGCC TCAGCTCTTC TGGTGGCCTC   4140

AGCTCTTCTA CCATCAAATA CACCACCACC TCCTCCAGCA AGAAGAGCTA CAGGCAGTGA   4200

ATTCTGTCAC CAAGAGCTTG TCTCTGGTCC CAGATGTCAT GGCTGCAGAA TCCTGTGCTC   4260

AGAGCCCCGA GTTCAGGGGC TTCTCCTCCC TGGACCCCAC CTCTGCTCCC TTCTTGGGAC   4320

TGAGGAGGCT GTGTCATTTT GCTCATATTT CTGTCCCCAT GGGTCCCCAC TGCTCATCTC   4380

TTTATAGTCA TCCTGTGAGC TTACATCACA ATTCACTCAC ATTTGGTGCT TCATGTTGTA   4440

TTTGGTTGCC AGGCTCCTGC CTCCCTACCT CTGTCTCTGA GGCTGCCTGT GACAGGGTGT   4500

TTCCGACACC TTCATTTTTG AAATCATTGT CTGGGTCCTA CTCAAGTAAT GAGCAGCTCC   4560

CTGTGAGTTT CTAATGGCCT GAGAAACCCC ATCTCTCAAC ATCATAACCC TCCCTGTCAG   4620

TAACTGTGAC TGCCCCGTCA CTGGTCCTGT GATGTAAGTT TCTGCTCATG TGATGTCTTT   4680

GCTTTCCTTG ATGCTCTTGG CTTCCTTGTA ATTTCTAAAT AAAGCAGGTT TATACATAAT   4740

AAAATTTTCC ACGTGCATTT TTTGTTGCAA TGTTTTTAAT ATAGAAATTC TGTGGCCTTG   4800

CTAGACAAGG CATCATTACA GTTCCCTCTC CCAGGTCTAT ATGTCTTCAT CTGTTAGTAT   4860

ATAGTTTAAA TTTAAGTTCA CATTTTAAAT TAATTTCAAT AACTTTTTAA ATAAAATAGA   4920

ATTCCATCAA TTCCCCCCCC TTCATTTTTC ACCTGCCCAG ATGTCTTCAC TCCAAACCCT   4980

CACCTGTTTC TCCATTTTCA AATTGAGAGT CTTTTGAGGA AGCCTATATT TCCTTCATTT   5040
```

```
TCTTATAAAT AATTTTGTAA TGTATCCATT TCCCTTTCTT TAAAGATAAT CAACAGATGT    5100

CAGTTCAGCG TTCCTTCCCA CATGAATTGC CTTCCTGTCA GCAAGAACAT GATCTGCAG     5159

(2) INFORMATION FOR SEQ ID NO:  4:

(i) SEQUENCE CHARACTERISTICS:
        (A) LENGTH:              16 amino acids
        (B) TYPE:                amino acid
        (C) STRANDEDNESS:        single
        (D) TOPOLOGY:            linear (ii) MOLECULE TYPE:          peptide (xi) SEQUENCE DESCRIPTION: SEQ ID NO: 4:

Cys Ser Ser Val Lys Phe Val Ser Thr Thr Tyr Ser Gly Val Thr Arg
1               5                   10                  15
```